US009927445B2

United States Patent
Rai et al.

(10) Patent No.: US 9,927,445 B2
(45) Date of Patent: *Mar. 27, 2018

(54) BIOMARKERS FOR PREDICTION, DIAGNOSIS, AND MONITORING OF PARKINSON'S DISEASE

(71) Applicants: Balwant Rai, Haryana (IN); Jasdeep Kaur, Punjab (IN)

(72) Inventors: Balwant Rai, Haryana (IN); Jasdeep Kaur, Punjab (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,125

(22) Filed: Jul. 7, 2014

(65) Prior Publication Data

US 2014/0322734 A1    Oct. 30, 2014

Related U.S. Application Data

(63) Continuation-in-part of application No. 14/081,544, filed on Nov. 15, 2013, now abandoned, which is a
(Continued)

(30) Foreign Application Priority Data

May 18, 2011 (IN) .......................... 1432/DEL/2011
Apr. 13, 2012 (IN) .......................... 1138/DEL/2012

(51) Int. Cl.
*G01N 33/53* (2006.01)
*G01N 33/543* (2006.01)
(Continued)

(52) U.S. Cl.
CPC . *G01N 33/6896* (2013.01); *G01N 2021/7786* (2013.01); *G01N 2333/525* (2013.01); *G01N 2333/545* (2013.01); *G01N 2333/65* (2013.01); *G01N 2333/926* (2013.01); *G01N 2800/2821* (2013.01); *G01N 2800/2835* (2013.01); *G01N 2800/52* (2013.01)

(58) Field of Classification Search
None
See application file for complete search history.

(56) References Cited

U.S. PATENT DOCUMENTS 6,780,645 B2 *  8/2004 Hayter et al. ................... 436/8
8,257,917 B2    9/2012 Wong et al.
(Continued)

OTHER PUBLICATIONS

Litteljohn et al., Chapter 8: Common Pathways to Neurodegeneration and Co-morbid Depression. M.S. Ritsner (ed.), Brain Protection in Schizophrenia, Mood and Cognitive Disorders, Feb. 10, 2010.*
(Continued)

*Primary Examiner* — Jeffrey J Stucker
*Assistant Examiner* — Aurora M Fontainhas
(74) *Attorney, Agent, or Firm* — Rylander & Associates, PC; Janina A. Malone; Philip R. M. Hunt

(57) ABSTRACT

A method for the risk detection, early diagnosis, prognosis, and monitoring of Parkinson's disease in an individual by measuring the amount of specific biomarkers present in a bodily fluid and comparing them to a reference level of biomarkers in a sample from a healthy person, a person previously diagnosed with Parkinson's disease, or an earlier sample from the individual of interest.

4 Claims, 1 Drawing Sheet

Related U.S. Application Data continuation of application No. 13/467,580, filed on May 9, 2012, now abandoned.

(51) Int. Cl.
  *G01N 33/68* (2006.01)
  *G01N 21/64* (2006.01)
  *G01N 21/93* (2006.01)
  *G01N 21/84* (2006.01)
  *G01N 21/77* (2006.01)

(56) References Cited

U.S. PATENT DOCUMENTS

| | | | |
|---|---|---|---|
| 2005/0221348 A1* | 10/2005 | Ray et al. | 435/6 |
| 2006/0018800 A1* | 1/2006 | Slowey | A61B 10/02 422/412 |
| 2007/0042437 A1 | 2/2007 | Wands et al. | |
| 2012/0112053 A1 | 5/2012 | Schneider | |

OTHER PUBLICATIONS

Suh et al., Salivary levels of IL-1b, IL-6, IL-8, and TNF-a in patients with burning mouth syndrome. a r c h i v e s of ora l b i o logy 54 (2009) 797-802.*

Devic et al., Salivary a-synuclein and DJ-1: potential biomarkers for Parkinson's disease. Brain 2011: 134; 1-5 | e178.*

Bermejo-Pareja et al., Saliva levels of Abeta1-42 as potential biomarker of Alzheimer's disease: a pilot study. BMC Neurology 2010, 10:108, 1-7.*

Kerr et al., Detection of Insulin and Insulin-Like Growth Factors I and II in Saliva and Potential Synthesis in the Salivary Glands of Mice. Biochemical Pharmcology, vol. 49, No. 10, pp. 1521-1531, 1995.*

Aydin, Comparison of Ghrelin, Glucose, Alpha-amylase and Protein Levels in Saliva from Diabetics. Journal of Biochemistry and Molecular Biology, vol. 40, No. 1, Jan. 2007, pp. 29-35.*

Abiko et al., The mechanism of protracted wound healing on oral mucosa in diabetes. Bosnian Journal of Basic Medical Sciences 2010; 10 (3): 186-191.*

Hansson et al: "Association between CSF biomarkers and incipient Alzheimer's disease in patients with mild cognitive impairment: a follow-up study", Lancet Neurology, 2006, vol. 5, Issue: 3, pp. 228-234.

Prolo P et al: "P3-103 Amyloid-beta, cytokine profiles and natural killer cell activity: supposed markers of Alzheimer's disease", Neurobiology of Aging, vol. 25, Jul. 1, 2004, p. S384.

Singhal R.K, Anand, S.: "Salivary-42, IGF-I, IGF-II, Alpha Amylase, IL-1, and TNF-alpha in Alzheimer's Disease: A Useful diagnostic tool", Aug. 3, 2013 (Aug. 3, 2013), Retrieved from the Internet: URL:https://web.archive.org/web/20140228131418; http://wwhttp://www.webmedcentral.com/wmcpdf/Article_WMC004358.pdf [retrieved on Mar. 12, 2014].

Singhal R.K, Anand, S.: "Salivary-42, IGF-I, IGF-II, Alpha Amylase, IL-1, and TNF-alpha in Alzheimer's Disease: A Useful diagnostic tool", Jan. 22, 2014 (Jan. 22, 2014), Retrieved from the Internet: URL:https://www.webmedcentral.com/article_view/4440; https://www.webmedcentral.com/wmcpdf/Article_with_review_WMC004440.pdf; https://www.webmedcentral.com/Article_Review_View/3032 [retrieved on Apr. 15, 2015].

Sappälä et al: "Plasma Ab42 and Ab40 as markers of cognitive change in follow-up: a prospective, longitudinal, population-based cohort study.", J. Neurol Neurosurg Psychiatry, vol. 10 No. 1136, May 2010.

Sayer et al: "Association of a salivary acetylcholinesterase with Alzheimer's disease and response to cholinesterase inhibitors", Clinical Biochemistry, vol. 37, Oct. 16, 2004, pp. 98-104.

Hoesel, Written Opinion of the International Searching Authority PCT/IB2013/001407, ISA/EPO, Germany.

Kim Chang-Beom et al: "Antibody-based magnetic nanoparticle immunoassay for quantification of Alzheimer's disease pathogenic factor.", J. Biomed. Optics, vol. 19, No. 5, May 2014, p. 51205.

German et al: "Serum biomarkers for Alzheimer's disease: Proteomic discovery", Biomedicine and Pharmacotherapy, vol. 61, No. 7, Aug. 15, 2007, pp. 383-389.

Boston Paul F et al: "Developing a simple laboratory test for Alzheimer's disease: measuring acetylcholinesterase in saliva—a pilot study", Int. J. Geriat. Psychiat., vol. 23, No. 4, Apr. 2008, pp. 439-440.

Alvarez et al: "Serum TNF-alpha levels are increased and correlate negatively with free IGF-I in Alzheimer disease", Neurobiology of Aging, vol. 28, No. 4, Feb. 23, 2007, pp. 533-536.

* cited by examiner

BIOMARKERS FOR PREDICTION, DIAGNOSIS, AND MONITORING OF PARKINSON'S DISEASE

CROSS-REFERENCE TO RELATED APPLICATION

This application is a continuation-in-part of U.S. patent application Ser. No. 14/081,544, filed Nov. 15, 2013, which is a continuation of U.S. patent application Ser. No. 13/467,580, filed May 9, 2012, which claims the benefit of co-pending Indian Patent Application Serial No. 1432/DEL/2011, filed 18 May 2011, and Indian Patent Application Serial No. 1138/DEL/2012, filed 13 Apr. 2012, all of which are herein incorporated by reference in their entirety.

FIELD OF THE INVENTION

The present invention relates to the detection and measurement of biomarkers. More specifically, the present invention relates to the detection and measurement of biomarkers for predicting, diagnosing, and monitoring neurological disorders including Parkinson's disease.

BACKGROUND

Despite the fact that cognitive impairment affects more than 16 million people in the United States alone (CDC Cognitive Impairment, A Call to Action Now! 2011), there are very few, if any, diagnostic laboratory tests that can clearly indicate the presence, absence, or type of neurodegenerative disease, and diagnoses are generally based on clinical evaluations of symptoms that occur late in the development of the disease. Further complicating the issue, many neurodegenerative diseases have overlapping symptoms making them difficult to diagnose and treat appropriately.

Alzheimer's disease (AD) is a progressive neurodegenerative disorder in which neurodegeneration starts decades before clinical symptoms appear (DeKosky S T, Marek K: "Looking Backward to Move Forward: Early Detection of Neurodegenerative Disorders," Science (2003) 302 (5646): 830-834). It is the most common cause of dementia in the elderly, accounting for 50-60% of all cases (Blennow K, de Leon M J, Zetterberg H: "Alzheimer's Disease": Lancet (2006); 368 (9533): 387-403) and it is believed that the number of people afflicted will reach over 100 million worldwide by 2050 (Ferri C P, Prince M, Brayne C, Brodaty H, Fratiglioni L, Ganguli M et al, "Global Prevalence of Dementia: a Delphi Consensus Study", Lancet (2005) 17; 366: 2112-7).

The symptoms of AD manifest slowly and the initial signs may only be mild forgetfulness. In this early stage, individuals have a tendency to forget recent events, activities, the names of familiar people or things and may not be able to solve simple mathematical problems.

As the disease progresses into moderate stages of AD, symptoms are more easily detected and become serious enough to cause people with AD or their family members to seek medical help. Moderate stage symptoms of AD include the inability to perform simple tasks such as grooming, and problems in speech, understanding, reading, and writing.

Severe stage AD patients may become anxious or aggressive, may wander away from home, and ultimately will need total care. While attempts have been made to create a diagnostic test using "multi-modal" methods combining the use of imaging techniques (e.g. PET scan, CT scan or MRI, for instance) with the detection of various biomarkers in cerebrospinal fluid (CSF) these methods are highly invasive, expensive, and have not been shown to be reliable in terms of sensitivity and specificity to detect AD accurately. The only definitive diagnostic currently available for AD is only employable post-mortem.

Parkinson's disease is a chronic, degenerative neurological disorder that affects one in 100 people over age 60. While the average age at onset is 60, some people are diagnosed at 40 or younger. Estimates of the number of people living with the disease vary, but recent research indicates that at least one million people in the United States, and more than five million people worldwide, have Parkinson's disease.

The cardinal symptoms of Parkinson's disease are resting tremor, bradykinesa and rigidity. To diagnose Parkinson's disease, doctors take a medical history and perform a thorough neurological examination. Doctors will also look for responsiveness to Parkinson's disease medications as further evidence that Parkinson's disease is the correct diagnosis. A DaTscan can be used to detect dopamine transporters in an individual suspected of having Parkinson's disease, but it is not a definitive test for Parkinson's disease. The lack of a definitive test for Parkinson's disease and the similarity of Parkinson's disease to other neurological conditions has led to a significant misdiagnosis rate with as many as 24% percent of cases being misdiagnosed (Rajput, 1991).

Despite advances in genomics in the last two decades, there is no objective test for Parkinson's disease, and Alzheimer's disease proteomics is still in its infancy. There is clearly an unmet need for diagnostic tests for neurological disorders such as Parkinson's and Alzheimer's disease.

SUMMARY

Provided herein is a non-invasive means for diagnosing, measuring and monitoring Alzheimer's disease (AD) and Parkinson's disease (PD) using a specific subset of one or more biomarkers. As disclosed herein, multiple biomarkers in the bodily fluids of an individual may be quantitatively measured alone or in combination as a diagnostic for AD or PD, including early diagnosis of AD or PD, as well as determiner of risk of developing AD or PD. Levels of biomarkers may also be used to monitor the progression and severity of AD or PD and determine the effectiveness of a particular treatment in arresting or reversing the progression of these neurological disorders.

The methods described herein include the identification of biomarkers such as proteins in a biological fluid, such as saliva. Such biomarkers may be identified by any means generally used by one of skill in the art. In some embodiments, these biomarkers are identified using antibody-based methods, such as, but not limited to, an enzyme-linked immunosorbant assay (ELISA), a radioimmunoassay (RIA), a lateral flow immunoassay, or proteomic approaches that utilize various detection methods.

Biomarkers as used herein may be one or more of $A\beta$-40, TNF-$\alpha$, IL-1-$\beta$, $A\beta$-42, IGF-I, IGF-II, Alpha-amylase, cTnI, Myoglobin, MMP-9, MMP-8, MMP-2, sICAM-1, Myeloperoxidase [MPO], IL-4, IL-5, B-type natiuretic peptide [BNP], IL-1$\alpha$, IL-11, IL-10, IFN-$\gamma$, VEGF, Insulin, GLP-1 (active), GLP-1 (total), TREM1, Leukotriene E4, Akt1, Fas ligand, PSA, G-CSF, MIP-1$\alpha$, IL-22, IL-8, IL-21, IL-15, IL-6, IL-7, GM-CSF, IL-2, IL-17$\alpha$, MCP, IL-32, RANTES, Apolipoprotein A1, Apolipoprotein D, Apolipoprotein E, Ischemia-modified albumin (IMA), Fibronectin, Aspartate aminotransferase, Lactate dehydrogenase, Tissue factor activity, MCP-1, sVCAM-1, and sCD-40. In some embodiments, biomarkers may be one or more of Aβ-40, TNF-α, IL-1-β, Aβ-42, IGF-I, IGF-II, and alpha-amylase. In some embodiments, biomarkers may be Aβ-40, Aβ-42 and one or more additional biomarkers selected from TNF-α, IL-1-β, IGF-I, IGF-II, and alpha-amylase.

The methods used herein include establishing reference levels for biomarkers in the bodily fluids of individuals. Such reference levels may be from a population of individuals who are cognitively normal, a population of individuals who have been diagnosed with AD or PD, or a previous sample from the individual currently being tested. These reference levels may be used as a comparison for biomarker levels in samples (such as saliva) obtained from an individual at risk for or suspected of having AD or PD. An individual is determined to be at risk for or have AD or PD if their biomarker levels are within reference levels of individuals with AD or PD or outside reference levels of biomarkers for a normal population. For example, reference levels for a diagnosis of AD generated from a population previously diagnosed with AD may be as follows: between about 2.8 to about 25.85 pg/ml for Aβ-40; about 143.3 to about 412.6 pg/ml for TNF-α, about 116.4 to about 291.8 pg/ml for IL-1 beta, about 4.6 to about 19.6 pg/ml for Aβ-42, about 0.35 to about 1.9 ng/ml for IGF-I, about 0.3 to about 2.51 ng/dl for IGF-II, and about 28.8 and 124.6 U/ml for alpha amylase. Reference levels for a diagnosis of PD generated from a population previously diagnosed with PD may be as follows: between about 19.9 to about 27.3 pg/ml for Aβ-40; about 67.4 to about 92.2 pg/ml for TNF-α, about 40 to about 92 pg/ml for IL-1 beta, about 3.4 to about 8.1 pg/ml for Aβ-42, about 0.9 to about 2.8 ng/ml for IGF-I, about 0.67 to about 4.2 ng/dl for IGF-II, and about 27.9 to about 49.5 U/ml for alpha amylase. Reference levels may additionally be smaller subsets of these ranges. For example, in some embodiments, reference levels for a diagnosis of AD generated from a population previously diagnosed with AD may be between about 10.8 to about 13.2 pg/ml for Aβ-40; about 154.8 to about 189.2 pg/ml for TNF-α, about 135 to about 165 pg/ml for IL-1 beta, about 4.68 to about 5.72 pg/ml for Aβ-42, about 1.56 to about 1.9 ng/ml for IGF-I, about 0.56 to about 0.68 ng/dl for IGF-II, and about 28.8 and 35.2 U/ml for alpha amylase. In additional embodiments, reference levels for a diagnosis of PD generated from a population previously diagnosed with PD may be as follows: between about 21.2 to about 25.9 pg/ml for Aβ-40; about 71.9 to about 87.9 pg/ml for TNF-α, about 60.8 to about 74.3 pg/ml for IL-1 beta, about 5.2 to about 6.4 pg/ml for Aβ-42, about 1.68 to about 2.06 ng/ml for IGF-I, about 2.21 to about 2.69 ng/dl for IGF-II, and about 34.9 and about 42.7 U/ml for alpha amylase. Biomarkers in an individual being tested for or at risk for AD or PD may be compared to one or more of these reference ranges.

In another embodiment the reference levels for biomarkers are established based on biomarker levels in a sample taken from an individual at an earlier point in time. The individual is determined to be responding to treatment for AD or PD if the relative amounts of the biomarkers in the biological sample have altered favorably from the biomarker levels in a biological sample taken at an earlier first time point from the same individual; i.e. trend towards normal biomarker levels. Similarly, the disease state of the individual may be progressing or remising if the biomarker levels in a biological fluid sample are changing relative to the levels in the individual taken at an earlier time point or in reference to the control levels.

The present invention further provides a kit for diagnosing, monitoring and predicting AD or PD. The kit includes: (a) a composition or panel of any one or more of the above identified biomarkers; (b) a substrate for holding a biological sample isolated from a human subject suspected of having AD or PD, being at risk for AD or PD, or being under treatment for AD or PD; (c) an agent that binds to at least one of the biomarkers; (d) a detectable label such as one conjugated to the agent, or one conjugated to a substance that specifically binds at least one or more of the biomarkers and provides a proportional response based on the level of biomarker present and (e) printed instructions for reacting the agent with the biological sample or a portion of the biological sample to detect the presence or amount of at least one marker in the biological sample and determining if the marker is within a reference level of the biomarker. For example, a kit may comprise a saliva sample obtained from the patient; a plurality of test strips, each configured to produce a fluorescence level proportional to a level present on the test strip of one of a group of biomarkers; and a reading device configured to read the fluorescence levels on each of the test strips after the test strips are exposed to the saliva sample and wherein when the fluorescence levels indicate that two or more of the biomarkers are between a reference level the patient is determined to have Parkinson's disease. In some embodiments, the kit may be used within the same time of day window, in the same manner and/or with the same test used to determine the reference levels.

These and other embodiments, features and potential advantages will become apparent with reference to the following description.

DETAILED DESCRIPTION

Figure 1:
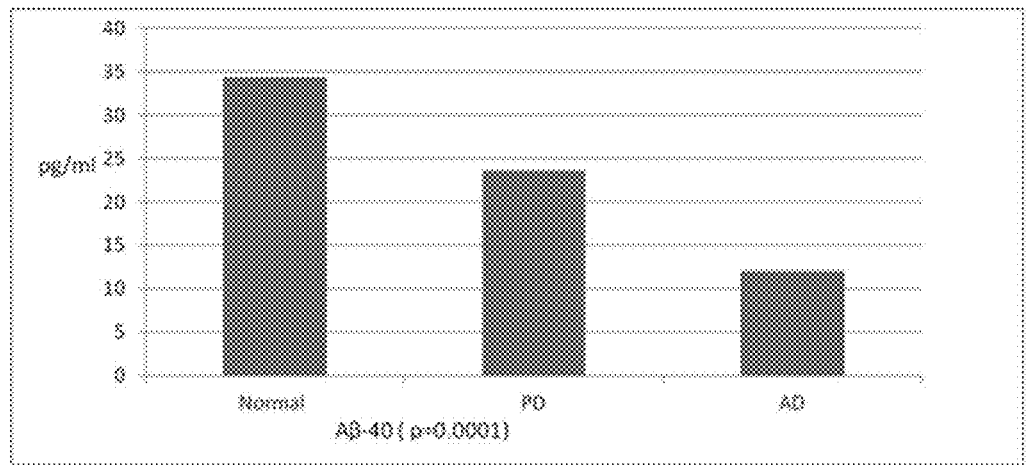
FIG. 1 is a graph comparing Aβ-40 levels in healthy individuals, individuals with AD, and individuals with PD.

Impairment of cognitive functions results in difficulties in coping with both complex and simple repetitive activities such as daily planning, working, managing finances, preparing food, keeping order, socializing, or pursuing interests. Unfortunately many cognitive impairment disorders have overlapping symptoms and can only be definitively diagnosed post-mortem making them difficult to diagnose and treat appropriately.

Alzheimer's disease (AD) is a severe neurodegenerative disorder of the brain characterized by progressive loss of memory and cognitive abilities. The majority of AD cases are sporadic with fewer than 2.5% having a genetic disposition. Currently, diagnosis is based on clinical assessment and post-mortem verification, however there is no definitive test available antemortem.

Parkinson's disease (PD) is a neurodegenerative disorder characterized by a progressive and relatively selective loss of anatomically or physiologically related neuronal systems (Lang and Lozano, 1998; Silvers and Som, 1998). Like AD, the majority of Parkinson's cases are sporadic with fewer than 15% having a genetic disposition. Currently diagnosis of Parkinson's disease requires a clinical assessment and there is no definitive test.

The lack of tools to detect preclinical AD and PD is one of the obstacles for the development of new treatments (Landsbury, 2004). The difficulty in accurately diagnosing AD and PD additionally leads to high rates of misdiagnosis, negatively impacting families and delaying or preventing treatment for treatable neurological disorders.

Previous attempts to identify and validate biomarkers for Alzheimer's disease in saliva have not been definitive, demonstrating differences in biomarker levels depending on the time of day collected, collection method used, and particular assay used for biomarker level detection. Described herein is the identification of relevant biomarkers and combinations of biomarkers useful for predicting, diagnosing, and monitoring AD and PD. The biomarkers may be particularly useful for diagnosing early stage AD or PD, allowing for earlier treatment options. The biomarkers disclosed herein may additionally be used as drug targets to develop new drugs as well as monitor different therapies for the treatment of AD and PD.

Definitions

"Alzheimer's patient" and "AD patient" each refers to an individual who has been diagnosed with AD. The individual may be diagnosed with AD by any means generally used by those of skill in the art. For example, they may be diagnosed through a Mini-Mental State Examination (MMSE, Folstein 1975), Diagnostic and Statistical Manual of Mental Disorders (DSM)-IV criteria (American Psychiatric Association: DSM-IV: Diagnostic and Statistical Manual of Mental Disorders, Washington D.C.: American Psychiatric Association (1994)) criteria, NINCDS-ADRDA criteria (McKhann G, Drachman D, Folstein M, Katzman R, Price D, Stadlan E M: "Clinical Diagnosis of Alzheimer's Disease: Report of the NINCDS-ADRDA Working Group Under the Auspices of the Department of Health and Human Services Task Force on Alzheimer's Disease," Neurology (1984) 34: 939-944)), or the Clinical Dementia Rating Scale (CDR) (Hughes, C. P., Berg, L., Danziger, W. L., et al (1982) *A New clinical scale for the staging of dementia*. British Journal of Psychiatry, 140, 566-572) or a combination thereof. For example, using the MMSE, scores of 27 or above (out of 30) are considered normal. An individual scoring between 21 and 26 points is viewed as having mild AD. An individual scoring between 10 and 20 points is viewed as having moderate AD and less than 10 points is rated as severe AD. On average people with Alzheimer's disease who do not receive treatment lose 2 to 4 points each year on the MMSE scoring system. AD patients may also be diagnosed postmortem.

"Parkinson's patient" and "PD patient" each refers to an individual who has been diagnosed with PD. The individual may be diagnosed with PD by any means generally used by those of skill in the art. Generally, PD is diagnosed by a neurological history and clinical exam for the cardinal symptoms of Parkinson's disease (resting tremor, bradykinesa and rigidity). Individuals may also be evaluated for postural instability and unilateral onset. In some instances, a physician may use Unified Parkinson's Disease Rating Scale (UPDRS) or the Movement Disorder Society's revised version of the UPDRS (Goetx, 2007). The modified UPDRS uses a four-scale structure with sub scales as follows: (1) non-motor experiences of daily living (13 items), (2) motor experiences of daily living (13 items), (3) motor examination (18 items) and (4) motor complications (6 items). Each subscale now has 0-4 ratings, where 0=normal, 1=slight, 2=mild, 3=moderate, and 4=severe. Clinicians may also use the criteria developed by the U.K. Parkinson's Disease Society Brain bank Clinical Diagnostic Criteria (Hughes A J, Daniel S E, Kilfor L, Lees A J. Accuracy of clinical diagnosis of idiopathic Parkinson's diseases. A clinic-pathological study of 100 cases. JNNP 1992; 55:181-184.) They may also use the Modified Hoehn and Yahr Scale (Hoehn M M, Yahr M D. Parkinsonism: onset, progression, and mortality. Neurology. 1967; 17:427-42.), Schwab and England Activities of Daily Living Scale (Schwab, R. S. & England, A. C. (1969). Projection technique for evaluating surgery in Parkinson's disease. In Third Symposium on in Parkinson's disease (ed. F. J. Gillingham and I. M. L. Donaldson), pp. 152±157. Livingstone: Edinburgh.), Abnormal Involuntary Movement Scale (AIMS, Guy W: ECDEU Assessment Manual for Psychopharmacology—Revised (DHEW Publ No ADM 76-338), US Department of Health, Education, and Welfare; 1976). Cognitive assessment may be made using the Mini Mental Status Exam (MMSE, Folstein M F, Folstein S E, McHugh P R (1975). ""Mini-mental state". A practical method for grading the cognitive state of patients for the clinician". *Journal of Psychiatric Research* 12 (3): 189-98. doi:10.1016/0022-3956(75)90026-6. PMID 120220), Montreal Cognitive Assessment (MoCA, Nasreddine, Z. S., Phillips, N. A., Bedirian, V., Charbonneau, S., Whitehead, V., Collin, I., Cummings, J. L., Chertkow, H., The Montreal Cognitive Assessment (MoCA): A Brief Screening Tool for Mild Cognitive Impairment www.mocatest.org) and the Clinical Dementia rating Scale (Morris, J. C. The Clinical Dementia Rating (CDR): Current vision and scoring rules Neurology, 1993; 43:2412-2414).

"Evaluate", "determinate", "discriminate" and "establish" are interchangeably used for diagnosis.

"Normal healthy" for AD refers to a value of zero on the clinical dementia rating scale (CRS) established by McKhann et al. (McKhann G, Drachman D, Folstein M, Katzman R, Price D, Stadlan E. "Clinical Diagnosis of Alzheimer's Disease: Report of the NINCDS-ADRDA Work Group Under the Auspices of the Department of Health and Human Services Task Force on Alzheimer's Disease. Neurology. 1984; 34: 939-944).

As used herein, the term "treatment" refers to the alleviation, amelioration, and/or stabilization of symptoms, as well as a delay in the progression of symptoms of a particular disorder through the use of some external drug, device or technology.

By "therapeutic effect," "therapeutic activity" or "therapeutic action" it is meant a desired pharmacological activity of the agent such as a reduction of one or more symptoms of AD or PD, a stabilization of one or more symptoms of AD or PD, a change in relevant biomarker levels for AD or PD or a combination thereof.

As used herein, a "reference value" of a biomarker can be an absolute value, a relative value, a value that has an upper and/or lower limit, a range of values, an average value, a median value, a mean value, a shrunken centroid value, a value as compared to a particular control or baseline value or a combination thereof. It is to be understood that other statistical variables may be used in determining the reference value. A reference value can be based on an individual sample value; for example, a value obtained from a sample from the individual with AD or PD, but at an earlier point in time, or a value obtained from a sample from an AD or PD patient other than the individual being tested, or a "normal" individual, that is an individual not diagnosed with AD or PD. The reference value can be based on a large number of samples, such as from AD patients or normal individuals or based on a pool of samples including or excluding the sample to be tested.

As used herein, "biomarker panel" refers to a set of biomarkers that can be used alone, together, or in subcombinations for the detection, diagnosis, prognosis, staging, or monitoring of a disease or condition, based on detection values for the set of biomarkers. The biomarkers within the panel of biomarkers used herein include Aβ-40, TNF-α, IL-1-β, Aβ-42, IGF-I, IGF-II, Alpha-amylase, cTnI, Myoglobin, MMP-9, MMP-8, MMP-2, sICAM-1, Myeloperoxidase [MPO], IL-4, IL-5, B-type natiuretic peptide [BNP], IL-1α, IL-11, IL-10, IFN-γ, VEGF, Insulin, GLP-1 (active), GLP-1 (total), TREM1, Leukotriene E4, Akt1, Fas ligand, PSA, G-CSF, MIP-1α, IL-22, IL-8, IL-21, IL-15, IL-6, IL-7, GM-CSF, IL-2, IL-17α, MCP, IL-32, RANTES, Apolipoprotein A1, Apolipoprotein D, Apolipoprotein E, Ischemia-modified albumin (IMA), Fibronectin, Aspartate aminotransferase, Lactate dehydrogenase, Tissue factor activity, MCP-1, sVCAM-1, and sCD-40. It will be appreciated that the specific identity of biomarkers within the panel and the number of distinct biomarkers within the panel can depend on the particular use to which the biomarker panel is put and the stringency that the results of panel must meet for the particular application.

As used herein, the term "time of day window" when referring to times that samples are taken means a period of time defined by a window start time and a window stop time. The terms "time of day window", "window start time", and "window stop time" all refer to local times where a sample was taken. The phrase "same time of day window" when referring to samples taken from multiple subjects means the same time of day window in local time, regardless of the time zone in which the sample is taken. For example, if one test subject is tested at 9:38 am local time in the +5 time zone and on the same day another subject is tested at 9:15 am local time in the −8 time zone, both samples are considered to have been taken in the same time of day window of 9 am-10 am, even though by Coordinated Universal Time, they were taken about 13 hours apart. Likewise, the samples taken in the foregoing example would be considered "within the same time of day window" even if they were taken at those times on different calendar days.

Methods for Predicting, Diagnosing, and Monitoring AD and PD

The compositions and methods described herein can be used in the prognosis, diagnosis, monitoring and treatment of AD or PD in an individual. Further described are compositions and methods for laboratory and point-of-care tests for measuring biomarkers in a sample from an individual.

The biomarkers and biomarker panels disclosed herein can be used in methods to screen subjects that have or are at risk for having PD or AD; to monitor individuals who are undergoing therapies for AD or PD; to differentially diagnose disease states associated with PD or AD; to evaluate the severity or progression of PD or AD in a patient; or to select or modify therapies or interventions for use in treating subjects with the disease.

In various embodiments described herein are methods for predicting the development of a disease in an individual, determining the prognosis of a disease in an individual, diagnosing a disease in an individual, or treating a disease in an individual by measuring the levels of biomarkers in an individual being monitored using a biomarker panel and comparing those to reference levels of biomarkers in a normal control, a population with AD or PD, and/or levels taken at a previous time point from the individual being monitored. In one aspect, the invention provides a method of diagnosing an individual with AD or PD comprising taking a biological sample from the individual, measuring the levels of biomarkers in a biomarker panel and correlating the measurement with the disease. In these embodiments, to make comparisons to the subject-derived sample, the amounts of reference biomarkers are similarly calculated. Subjects identified as having AD or PD, or at increased risk of developing a disease may receive therapeutic treatments to slow the progression of the disease or prevent the risk of developing a disease. A disease is considered to be progressive if the amount of biomarker moves further away from a reference level over time, whereas a disease is not progressive if the amount of biomarkers remains constant over time, approaches the reference level of a healthy individual, and/or if the symptoms of the individual with AD or PD stabilize or improve.

The use of biomarkers allows for real-time testing to predict, diagnose and monitor disease and treatment of AD and PD. Measurement of any combination of biomarkers described herein may be used to assemble a biomarker panel. The combination may refer to the measurement of an entire set or any subset or sub-combination of biomarkers thereof. Specifically, the detection of a plurality of biomarkers in a sample can increase the sensitivity and/or specificity of the test. Thus, in various embodiments, a biomarker panel as described herein may be used to measure 1, 2, 3, 4, 5, 6, 7, 8, 9, 10, 11, 12, 13, 14, 15, 16, 17, 18 or more biomarkers. In exemplary embodiments, a biomarker panel may measure 1, 2, 3, 4, 5, 6, or 7 biomarkers. Relevant biomarkers for the predicting, diagnosing and monitoring of AD and PD include Aβ-40, TNF-α, IL-1-β, Aβ-42, IGF-I, IGF-II, Alpha-amylase, cTnI, Myoglobin, MMP-9, MMP-8, MMP-2, sICAM-1, Myeloperoxidase [MPO], IL-4, IL-5, B-type natiuretic peptide [BNP], IL-1α, IL-11, IL-10, IFN-γ, VEGF, Insulin, GLP-1 (active), GLP-1 (total), TREM1, Leukotriene E4, Akt1, Fas ligand, PSA, G-CSF, MIP-1α, IL-22, IL-8, IL-21, IL-15, IL-6, IL-7, GM-CSF, IL-2, IL-17α, MCP, IL-32, RANTES, Apolipoprotein A1, Apolipoprotein D, Apolipoprotein E, Ischemia-modified albumin (IMA), Fibronectin, Aspartate aminotransferase, Lactate dehydrogenase, Tissue factor activity, MCP-1, sVCAM-1, sCD-40. In some embodiments, biomarkers may be one or more of Aβ-40, TNF-α, IL-1-β, Aβ-42, IGF-I, IGF-II, and alpha-amylase. In some embodiments a single biomarker may be measured. In other embodiments a biomarker panel may be used to measure one or more of the listed biomarkers in any combination. In further embodiments a biomarker panel may be used to measure levels of Aβ-40. In another embodiment, a biomarker panel may be used to measure levels of Aβ-40 and Aβ-42. In a further embodiment, a biomarker panel may be used to measure levels of Aβ-40 and Aβ-42 and one or more additional biomarkers. In a further embodiment, a biomarker panel may be used to measure levels of IGF-II, Aβ-40 and Aβ-42. In an additional embodiment, a biomarker panel may be used to measure levels of IGF-I, IGF-II, Aβ-40 and Aβ-42. In yet another embodiment, a biomarker panel may be used to measure levels of IL-1β, IGF-I, IGF-II, Aβ-40 and Aβ-42. In a further embodiment, a biomarker panel may be used to measure levels TNFα, IGF-I, IGF-II, Aβ-40 and Aβ-42. In yet another embodiment, a biomarker panel may be used to measure levels of IL-1β, TNF-α, IGF-I, IGF-II, Aβ-40 and Aβ-42. In another embodiment, a biomarker panel may be used to measure levels of IL-1β, TNF-α, IGF-I, IGF-II, Aβ-40, alpha amylase and Aβ-42. The biomarkers of the invention show a statistically significant difference in individuals with AD or PD and healthy controls and between AD and PD as shown in Tables 4 and 9, below. In various embodiments, diagnostic tests that use these biomarkers alone or in combination show a sensitivity and specification of at least about 80%, at least about 82%, at least about 85%, at least about 89%, at least about 90%, at least about 92%, at least about 94%, at least about 95%, at least about 96%, and about 100%. Biomarkers as described herein may be used alone or in combination with other diagnostic tools.

A good biomarker should be (a) precise, reliable and inexpensive, while detecting a fundamental feature of the neuropathology, (b) be validated in neuropathologically confirmed cases, (c) be non- or minimally invasive and (d) have marker specificity high enough to distinguish between neurodegenerative diseases. (German, et al., Serum biomarkers for Alzheimer's disease: proteomic discovery. Biomedicine & Pharmacotherapy, 61 (2007) 383-389). Additionally, sets of biomarkers may be used to increase the sensitivity of tests to predict, monitor and diagnose AD and PD. Sets may comprise one, two, three, four, five, six, seven or more biomarkers. These sets of biomarkers are useful for a number of purposes, for example, determining the risk of developing AD or PD, assessing the severity of the disease, monitoring AD or PD post-diagnosis, monitoring the effectiveness of therapeutic treatments and others. In other embodiments, ratios of biomarkers to each other may be useful in predicting, diagnosing and monitoring AD and PD.

Biomarkers may be collected using any means generally used from any bodily fluid including, but not limited to, saliva, blood, gingival crevicular fluid, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, and suspect tissues or any other constituents of the body which may contain the target molecule of interest. As described herein, assessment of results may be qualitative or quantitative depending upon the specific method of detection employed.

While biomarkers may be identified from any bodily fluid, human saliva collection is less invasive than that of blood for serum/plasma analyses and many, if not all, blood components are reflected in saliva. Saliva is the product of three pairs of major salivary glands, parotid (PAR), submandibular (SM) and sublingual (SL), and multiple minor salivary glands lying beneath the oral mucosa. Saliva is an attractive diagnostic fluid because salivary testing is low cost, non-invasive, and easy to collect and process. For example, saliva may be collected by stimulated or unstimulated means as described in Example I, below. In some embodiments, the saliva collecting device may comprise an absorbent pad material that is made up of hydrophilic materials from a list including Ahlstrom materials catalog numbers 270 and 320, Schleicher & Schuell catalog numbers 300 and 900 and Filtrona Fibertec Transorb Wicks, among others. Experimentation has shown that a large cross-section of substances to be detected or measured in fluids can be carried out using one of these versatile products. Hydrophobic pad materials may not adequately "wet" in aqueous solutions but will be wetted in low surface tension liquids such as alcohols, and may require the addition of, for example, low alcohol concentrations in the buffering system.

Those skilled in the art know that absorbent pad materials may also include hydrophilic or hydrophobic components bound, or integrated into the material, such components being capable of modifying the absorption and release characteristics of the absorbent pad as well as the speed of uptake of the sample fluid under consideration. In other embodiments, the saliva collection agent may be made out of a mixture of polyethylene and polypropylene such as those described in U.S. Pat. No. 7,618,591 and U.S. Pat. No. 8,025,851.

Various saliva collection devices which may be used for stimulated or unstimulated saliva collection. For example, the UltraSal-2™ (Oasis Diagnostics) saliva collection device, is for the collection of oral fluid/saliva samples. It automatically splits the saliva specimen into two aliquots in separate collection tubes. One tube can be used for testing while the second may be used for confirmation of results or for future use. No absorbent is involved in this method. The specimen is collected by holding the mouth piece between the lips and expectorating the oral fluid through the hole in the mouth piece into the collection tubes. The process is stopped when there is sufficient specimen collected. The collection tubes are capped and the mouthpiece is discarded. The volume collected is up to the capacity of the tube; the volume recovered is 100% of the collected volume. The Versi-SAL® (Oasis Diagnostics) as described in U.S. Pat. No. 7,618,591, is a fluid collection device that incorporates a proprietary interchangeable absorbent pad. It works by placing the device pad under the tongue and collecting saliva until a sample sufficiency indicator is triggered, usually after 1-2 minutes. The collector is then pushed down into a supplied compression tube until the pad is significantly compressed to release the absorbed saliva. The saliva specimen is forced through an outlet into a graduated tube. Recovery efficiency is about 60%. In the Salivette® (Sarstedt) device, saliva collection is carried out by chewing a cotton wool swab. Recovery of the saliva sample is achieved by returning the swab to the Salivette® tube and centrifuging the container. The volume collected is 1.7 ml; the volume recovered is 1.4 ml (82%). In the Intercept (STC) device, a pad is swabbed in the mouth for 2 to 5 minutes, the pad is inserted into a vial and snapped off at a scoring, and the vial is capped and sealed. Others devices mentioned in the literature, including: Ora Sure (Epitope), Saliva Sampler (Saliva Diagnostics) and ORALscreen collector (Avitar).

The VerOFy® (Oasis Diagnostics), as described in U.S. Pat. Nos. 7,618,591 and 7,927,548, both of which are incorporated by reference herein in their entireties, incorporates rapid and standardized saliva collection with immunochromatographic test strips providing a system for delivery of immediate results in the field or at point-of-care locations. The various biomarkers are conjugated to a Europium bead that emits fluorescence that is proportional to each of the biomarkers present in the saliva sample.

Biomarkers in a biological sample such as saliva can generally be measured and detected through a variety of assays, methods and detection systems known to those of skill in the art. The term "measuring", "detecting," or "taking a measurement" refers to a quantitative or qualitative determination of the amount or concentration of the biomarker in a particular sample. The term "concentration" or "level" can refer to an absolute or relative quantity.

The biomarkers used herein to predict, diagnose, or monitor PD or AD may be measured using any process known to those of skill in the art including, but not limited to, enzyme linked immunosorbent assay (ELISA), fluorescence polarization immunoassay (FPIA) and homogeneous immunoassays, point of care tests using conventional lateral flow immunochromatography (LFA), quantitative point of care tests using determination of chemiluminescence, fluorescence, and magnetic particles, as well as latex agglutination, biosensors, gel electrophoresis, mass spectrometry (MS), gas chromatograph-mass spectrometry (GC-MS), and nanotechnology based methods, by way of example. This technology includes qualitative or quantitative measurement of levels of AD and PD biomarkers in a biological sample such as saliva. Such technologies include immunofluorescent assays, enzyme immunoassays, radioimmunoassays, chemiluminescent assays, sandwich-format assays, techniques using microfluidic or MEMS technologies, re-engineering technologies (e.g. instruments utilizing sensors for biomarkers used for telemedicine purposes), epitope-based technologies, other fluorescence technologies, microarrays, lab-on-a-chip, and rapid point-of-care screening technologies. For example, as shown in Example II, below, biomarkers may be identified using an ELISA test specific for the biomarker(s) of interest which generates a color change that can be measured using a spectrophotometer.

In some embodiments, devices used to measure one or more biomarkers may be pretreated with magnetic particles, nanoparticles or one of a series of other molecules coated with a substance or molecule capable of specifically or non-specifically binding to components in the saliva thereby improving the performance of the assay by blocking or obstructing interfering substances.

Saliva samples may be collected using the same, different, or similar types of collection methods to those used for prior collections and/or in comparison to collection methods used for reference levels. As different types of collection methods may yield different biomarker levels, in some embodiments, all saliva samples may be collected in the same manner. For example, the original sample and repeat samples may be collected using the same type of collection method used in determining the reference levels.

As seen in E. A. Shirtcliff et al., Psychoneuroendocrinology 26 (2001) 165-173, "[i]mmunoassay results for salivary testosterone, DHEA, progesterone, and estradiol are higher, whereas sIgA results are significantly lower, when samples are collected using cotton absorbent materials compared to samples collected without cotton." "In samples collected using the polypropylene Salivette cortisol, cortisol AOPP concentrations were lower (by 60%) in comparison to measurements in whole unstimulated saliva." Kamodyová N, Celec P., Salivary markers of oxidative stress and Salivette collection systems. Clin Chem Lab Med. 2011 November; 49(11):1887-90. doi: 10.1515/CCLM.2011.677. Epub 2011 Aug. 23.

Additionally, "the cotton roll collection method affects the results of total protein, s-IgA, amylase and cortisol" T.-L. Li and M. Gleeson. The cotton swab method for human saliva collection: effect on measurements of saliva flow rate and concentrations of protein, secretory immunoglobulin A, amylase and cortisol. University College London (2003) J Physiol 547P, PC5.

Therefore, in some embodiments, initial, control, repeat and reference samples may be collected using the same or the same type of saliva collection method. In other embodiments, they may be collected using different collection methods.

Along with collection methods, biomarker levels can additionally be affected by a number of other factors including, but not limited to, gender, measurement of saliva flow rates, collection location, oral inflammatory disease, smoking, screening questions, circadian rhythms, blood and environmental contamination, certain medications, and stability during storage. (Shirtcliff E A, Granger D A, Schwartz E, Curran M J. Use of salivary biomarkers in biobehavioral research: cotton-based sample collection methods can interfere with salivary immunoassay results. Psychoneuroendocrinology. 2001 February; 26(2):165-73; Tomoaki Kozaki, Soomin Lee, Takayuki Nishimura, Tetsuo Katsuura, Akira Yasukouchi, Effects of saliva collection using cotton swabs on melatonin enzyme immunoassay Journal of Circadian Rhythms 2011, 9:1; Roslinda Mohamed, Jennifer-Leigh Campbell, Justin Cooper-White, Goce Dimeski, and Chamindie Punyadeera, The impact of saliva collection and processing methods on CRP, IgE, and Myoglobin immunoassays, Mohamed et al. Clinical and Translational Medicine 2012, 1:19; T.-L. Li and M. Gleeson, The cotton swab method for human saliva collection: effect on measurements of saliva flow rate and concentrations of protein, secretory immunoglobulin A, amylase and cortisol, University College London (2003) J Physiol 547P, PC5; Ohshiro K, Rosenthal D I, Koomen J M, Streckfus C F, Chambers M, Kobayashi R, El-Naggar A K. Pre-analytic saliva processing affect proteomic results and biomarker screening of head and neck squamous carcinoma. Int J Oncol. 2007 30 (3): 743-9; Wiviott S D, Cannon C P, Morrow D A, Murphy S A, Gibson C M, McCabe C H, Sabatine M S, Rifai N, Giugliano R P, DiBattiste P M, Demopoulos L A, Antman E M, Braunwald E. Differential expression of cardiac biomarkers by gender in patients with unstable angina/non-ST-elevation myocardial infarction: a TACTICS-TIMI 18 (Treat Angina with Aggrastat and determine Cost of Therapy with an Invasive or Conservative Strategy-Thrombolysis In Myocardial Infarction 18) substudy. Circulation 2004; 109:580-586; Keller M, et al. (2009) A circadian clock in macrophages controls inflammatory immune responses. Proc Natl Acad Sci USA 106:21407-21412; David Soo-Quee Koh, Gerald Choon-Huat Koh, The use of salivary biomarkers in occupational and environmental medicine, Occup Environ Med. March 2007; 64(3): 202-210). For example, as shown in Example IV and Table 6, below, there is a difference in the concentration of biomarkers depending on the type of collection method used. While the difference was determined to not be significant in tests for IGF-I, IGF-11, Aβ-40, Aβ-42, alpha amylase, Il-1 beta and TNF-alpha, biomarker levels are lower in stimulated saliva compared to samples collected using a drooling technique. Care is therefore needed to compare the results of the sample analysis with a reference collected using the same method. In some embodiments, reference levels as used herein may be from an age-matched population, a degenerative control population, a non-AD neurodegenerative control population, a healthy age-matched control population, a gender-matched control population, a sample time matched population or a combination thereof. In additional embodiments, sample analysis may be compared to reference levels taken within the same time of day window. In further embodiments, sample analysis may be compared to reference levels of individuals with the same or similar genetic profiles, for example reference levels may be collected from individuals who carry the Apo E ϵ4 isoform.

The methods used herein include establishing reference levels for biomarkers. The reference levels may be established from individuals who do not have cognitive impairment, individuals who do have AD or PD, or from the individual of interest. These reference levels may be used as a comparison for biomarker levels in samples (such as saliva) obtained from an individual at risk for AD or PD, suspected of having AD or PD, or under treatment for AD or PD. In some examples, the control is a sample from a subject not known to have cognitive impairment or decline. The individual is determined to be at risk for or have AD or PD if the biomarker levels are statistically different in relative amounts to the biomarkers in the biological sample of a healthy control. The individual is determined to be at risk for or have AD or PD if the biomarker levels are statistically equivalent to the biomarker levels in a population previously diagnosed with AD or PD. The individual is determined to be responding to treatment for AD or PD if the relative amounts of the biomarkers in the biological sample have altered from the biomarkers in a biological sample taken at an earlier first time point from the individual. The disease state of the individual may be progressing if the biomarker levels in a biological fluid are changing relative to the levels in the individual taken at an earlier time point.

In some embodiments, the measured value of an individual at risk for, suspected of having AD or PD, or being treated for AD or PD may be diagnosed by calculating the number of fold differences (i.e. 2-fold, 3-fold, etc.) between the measured value in the individual and the reference value. A fold difference can additionally be a value in the range of 10% to 90% of the reference value. In other embodiments, a fold difference can be determined by measuring the absolute concentration of a biomarker and comparing that to the absolute value of a reference. Alternately, a fold difference can be measured as the relative difference between a reference value and a sample value, where neither value is a measure of absolute concentration, and/or where both values are measured simultaneously. In other embodiments, the fold difference between the measured value in the individual and the reference value may be compared to a minimum fold difference. In additional embodiments the measured levels in a particular individual may be normalized against values from normal, healthy individuals. In further embodiments, the measured levels for a particular individual may be compared to reference levels for healthy individuals and reference levels of individuals previously diagnosed with AD or PD. For example, reference levels for a diagnosis of AD generated from a population previously diagnosed with AD may be as follows: between about 2.8 to about 25.85 pg/ml for Aβ-40; about 143.3 to about 412.6 pg/ml for TNF-α, about 116.4 to about 291.8 pg/ml for IL-1 beta, about 4.6 to about 19.6 pg/ml for Aβ-42, about 0.35 to about 1.9 ng/ml for IGF-I, about 0.3 to about 2.51 ng/dl for IGF-II, and about 28.8 and 124.6 U/ml for alpha amylase. Reference levels for a diagnosis of PD generated from a population previously diagnosed with PD may be as follows: between about 19.9 to about 27.3 pg/ml for Aβ-40; about 67.4 to about 92.2 pg/ml for TNF-α, about 40 to about 92 pg/ml for IL-1 beta, about 3.4 to about 8.1 pg/ml for Aβ-42, about 0.9 to about 2.8 ng/ml for IGF-I, about 0.67 to about 4.2 ng/dl for IGF-II, and about 27.9 and about 49.5 U/ml for alpha amylase. Reference levels may additionally be smaller subsets of these ranges. For example, in some embodiments, reference levels for a diagnosis of AD generated from a population previously diagnosed with AD may be between about 10.8 to about 13.2 pg/ml for Aβ-40; about 154.8 to about 189.2 pg/ml for TNF-α, about 135 to about 165 pg/ml for IL-1 beta, about 4.68 to about 5.72 pg/ml for Aβ-42, about 1.56 to about 1.9 ng/ml for IGF-I, about 0.56 to about 0.68 ng/dl for IGF-II, and about 28.8 and 35.2 U/ml for alpha amylase. In additional embodiments, reference levels for a diagnosis of PD generated from a population previously diagnosed with PD may be as follows: between about 21.2 to about 25.9 pg/ml for Aβ-40; about 71.9 to about 87.9 pg/ml for TNF-α, about 60.8 to about 74.3 pg/ml for IL-1 beta, about 5.2 to about 6.4 pg/ml for Aβ-42, about 1.68 to about 2.06 ng/ml for IGF-I, about 2.21 to about 2.69 ng/dl for IGF-II, and about 34.9 and about 42.7 U/ml for alpha amylase. An individual may be diagnosed as having AD or PD if their biomarker levels fall within one or more of these ranges.

Results of the quantification of various biomarker levels in the saliva of AD patients, lead to the differentiation of a priority listing of biomarkers (clustered by the methods described herein as shown in Examples II, VI, and IX) in decreased ranking order with the highest to lowest ranked biomarkers within each cluster ranked based on values that are shown to be significantly elevated or significantly decreased in AD patients compared to age-matched normal healthy controls and against other neurodegenerative diseases that are not AD, such as for example Parkinson's disease ("PD") and PN (neurodegenerative diseases that are not AD or PD) compared to all control samples. Generally, a significant increase or decrease in the level of a given biomarker compared to an appropriate control may be indicative of AD.

As shown in Table 3 of Example 2, below, different levels of salivary IGF-I, IGF-II, Aβ-40, Aβ-42, alpha amylase, IL-1 beta and TNF-alpha biomarkers were demonstrated to be useful in discriminating AD patients from controls. IGF-I, IGF-II, Aβ-40, Aβ-42, alpha amylase, IL-1 beta and TNF-alpha biomarkers were also demonstrated to be useful in discriminating between the different severities of Alzheimer's disease as shown in Table 4 and Table 23 below with sensitivities and specificities of the individual biomarkers reaching as high as 90% for individual biomarkers (Table 5) and 95% sensitivity and 96.2% specificity for combinations of biomarkers (Table 11). Additionally, the data was reproducible as shown in Table 18 Therefore salivary biomarkers, and specifically IGF-I, IGF-II, Aβ-40, Aβ-24, alpha amylase, IL-1 beta and TNF-alpha biomarkers are effective in predicting, diagnosing and monitoring of AD.

As shown in Example VI, different levels of salivary IGF-I, IGF-II, Aβ-40, Aβ-42, alpha amylase, IL-1 beta and TNF-alpha biomarkers were demonstrated to be useful in discriminating PD patients from controls with sensitivities and specificities of the individual biomarkers reaching as high as 89% and 95% for individual biomarkers (Table 10) and 95 and 96.2% sensitivity and for combinations of biomarkers (Table 11). Therefore salivary biomarkers, and specifically IGF-I, IGF-II, Aβ-40, Aβ-42, alpha amylase, IL-1 beta and TNF-alpha biomarkers are effective in predicting, diagnosing and monitoring of PD.

The identified biomarkers vary significantly within the subsets and possess the optimum characteristics for diagnostic/prognostic purposes for the diagnosis, monitoring, and/or prediction of AD and PD. In some embodiments, the individual biomarkers may be used to predict, monitor and diagnose AD and PD. For example, as shown in Table 4 and Table 18, below, levels of the marker, Aβ-42 are increased in AD patients with a questionable AD diagnosis (MMSE=27-30) and that quantitative levels of Aβ-42 are increased in AD patients with mild AD (MMSE=20-25).

Biomarkers may be measured individually or as part of a panel of biomarkers. In some embodiments, biomarkers for AD and PD are attached to a surface such that levels might be obtained directly or indirectly. In further embodiments, AD and PD biomarker-specific affinity reagents are bound to a solid support to provide separation of the AD and PD biomarkers in biological samples particularly saliva. AD and PD biomarker complex formation leads to at least one AD and PD diagnostic biomarker bound to a reagent specific for the biomarker, wherein said biomarker is attached to a surface. Binding or complex formation can be estimated qualitatively or quantitatively. Both standard and competitive formats for these assays including point of care systems are known in the art. The bound AD and PD biomarkers are detected using a mixture of appropriate detection reagents, which includes fluorescent dye-based or other visual systems that specifically bind various AD and PD biomarkers.

In a further embodiment, the present invention may be a biochip assay, a composition generally comprising a solid support or substrate to which a capture binding ligand is attached and can bind to proteins. Detection of a target species in some embodiments requires a label or detectable marker that can be incorporated as generally known to those of skill in the art. Such labels may be isotopic labels; magnetic, electrical or thermal labels; colored or luminescent dye; and enzymes, all of which enable detection of the biomarkers. In various embodiments, a secondary detectable label is used. A secondary label is one that is indirectly detected including, but not limited to, one of a binding partner pair; chemically modifiable moieties; nuclease inhibitors; enzymes such as horseradish peroxidase, alkaline phosphatases, luciferases etc. In sandwich formats of the invention, an enzyme serves as the secondary label, bound to the soluble capture ligand. In various embodiments, the system relies on detecting the precipitation of a reaction product or on a change on the properties of the label, for example the color for detection. A detection system for colorimetric methods includes any device that can be used to measure colorimetric properties. Generally, the device is a spectrophotometer, a colorimeter, or any device that measures absorbance or transmission of light on one or more wavelengths.

The present invention further provides a kit for diagnosing, monitoring, and predicting AD or PD. The kit includes (a) a composition or panel of biomarkers as identified by anyone or more of the biomarkers listed above (b) a substrate for holding a biological sample isolated from a human subject suspected of having AD or PD, being at risk for AD or PD or being under treatment for AD or PD; (c) an agent that binds to at least one of the biomarkers; (d) a detectable label such as one conjugated to the agent, or one conjugated to a substance that specifically binds at least one or more of the biomarkers and generates a signal proportionate to the amount of biomarker in the sample and (e) printed instructions for reacting the agent with the biological sample or a portion of the biological sample to detect the presence or amount of at least one marker in the biological sample and determining whether the maker falls within a reference level. For example, a kit may comprise a saliva sample obtained from the patient; a plurality of test strips, each configured to produce a fluorescence level proportional to a level present on the test strip of one of a group of biomarkers; and a reading device configured to read the fluorescence levels on each of the test strips after the test strips are exposed to the saliva sample and wherein when the fluorescence levels indicate that two or more of the biomarkers are between a reference level the patient is determined to have Parkinson's disease. In some embodiments, the kit may be used within the same time of day window, in the same manner and/or with the same test used to determine the reference levels.

The terminology used herein is for the purpose of describing particular embodiments only and is not intended to be limiting of the invention. As used in this document, the singular forms "a," "an," and "the" include plural references unless the context clearly dictates otherwise. Unless defined otherwise, all technical and scientific terms used herein have the same meanings as commonly understood by one of ordinary skill in the art.

Examples

The following studies are provided to illustrate the invention, but are not intended to limit in any way the scope of the invention. Provided herein is the determination of a panel of biomarkers in human whole saliva (WS) and stimulated saliva useful in the prediction, diagnosing and monitoring of neurodegenerative diseases such as Alzheimer's disease and Parkinson's disease. Biomarkers were measured using RIA and ELISA tests and biomarkers were evaluated for utility in discriminating AD and PD patients from normal controls.

Example I

Identification of Patient Population for the Determination of Alzheimer's Disease Markers in Saliva In order to obtain a population of Alzheimer's Disease patients and a demographically matched control group, individuals from three rural clinics in Punjab, India complaining of loss of memory and their family and caregivers were evaluated using the criteria of the Diagnostic and Statistical Manual of Mental Disorders (DSM)-IV (American Psychiatric Association: *DSM-IV. Diagnostic and Statistical Manual of Mental Disorders*. Washington D.C.: American Psychiatric Association; 1994), the Clinical Dementia Rating Scale (CDR) (Hughes, C. P., Berg, L., Danziger, W. L., et al (1982) A new clinical scale for the staging of dementia. *British Journal of Psychiatry,* 140, 566-572.), the mini-mental state examination (MMSE) (Folstein M F, Folstein S E, McHugh P R: "Mini-mental state." A practical method for grading the cognitive state of patients for the clinician. *J Psychiatr Res* 1975, 12:189-198), the NINCDS-ARDA criteria ((McKhann G, Drachman D, Folstein M, Katzman R, Price D, Stadlan E M: Clinical diagnosis of Alzheimer's disease: report of the NINCDS-ADRDA Work Group under the auspices of Department of Health and Human Services Task Force on Alzheimer's Disease. *Neurology* 1984, 34:939-944), the clinical Dementia Rating (CDR) scale (Hughes et al., 1982), consensus guidelines for the clinical and pathologic diagnosis of dementia with Lewy bodies (DLB): report of the consortium on DLB international workshop (McKeith, I. G., Galasko, D., Kosaka, K., et al (1996) *Neurology,* 47, 1113-1124), the Clinical Dementia Rating Scale (Hughes, C. P., Berg, L., Danziger, W. L., et al (1982) *A New clinical scale for the staging of dementia*. British Journal of Psychiatry, 140, 566-572) the Cambridge Cognitive Examination (CAM-COG) (Roth M, Tym E, Mountjoy Cq, Huppert F A, Hendrie H, Verma S, et al. CAMDEX. A standardized instrument for the diagnosis of mental disorder in the elderly with special reference to the early detection of dementia. Br J Psychiatry 1986; 149: 698-709 and Huppert, F. A., Brayne, C., Gill, C., Paykel, E. S., & Beardsall, L. (1995). CAMCOG—a concise neuropsychological test to assist dementia diagnosis: socio-demographic determinants in an elderly population sample. Br. J. Clin. Psychol. 34 (Part 4), 529-541)); the Geriatric Depression Scale (GDS) (Yesavage J A, Brink T L, Rose T L, Lum O, Huang V, Adey M, Leirer V O. Development and validation of a geriatric depression screening scale: a preliminary report. J Psychiatr Res. 1982-1983; 17(1):37-49.)); Bristol Activities of Daily Living (Bucks R S, Ashworth D L, Wilcock G K, Siegfried K. Assessment of activities of daily living in dementia: development of the Bristol Activities of Daily Living Scale. Age Ageing. 1996 March; 25(2): 113-20.)) and the Functional Activities Questionnaire (FAQ)

(Pfeffer R I, Kurosaki T T, Harrah C H Jr, Chance J M, Filos S. Measurement of functional activities in older adults in the community. J Gerontol. 1982 May; 37(3):323-9.)).

In order to be included in the study, the patients had to meet the DSM-IV criterion for Alzheimer's Disease (DSM-IV-TR™ Code Number: 294.1x, 1994), the NINCDS/ADRDA criterion for "probable" or "possible" Alzheimer's disease (McKhann G et al., *Neurology* 1984, 34:939-944) and score at least one on the Clinical Dementia Rating Scale (Hughes, C. P. et al., British Journal of Psychiatry, 140, 566-572). Individuals were further evaluated using a core battery of tests as described in Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. *Archives of Neurology,* 49, 453-460. Individuals were classified as having mild Alzheimer's Disease (MMSE 21-26, n=35), Moderate Alzheimer's Disease (MMSE 10-20, n=37), or severe Alzheimer's Disease (MMSE less than 10, n=28).

Individuals were excluded if they met the NINCDS/ADRDA criterion for vascular dementia (McKhann G et al., *Neurology* 1984, 34:939-944), dementia with Lewy bodies, Non-AD dementia (i.e., frontal lobe dementia, Creutzfelxt-Jakob disease, Huntington's disease) and any other concomitant disease such as diabetes, hypertension, cardiovascular disease and vascular diseases.

Members of the control group had to match the demographics of the patients with Alzheimer's disease. They additionally could not be known to suffer from dementia or other systemic diseases, score more than 24 on the MMSE, or score less than 1 on the CDR scale. The control group was additionally evaluated using the CAMCOG and the Functional Activities Questionnaire. Both patients and members of the control group were monitored for depression using the Geriatric Depression Scale where normal was defined as a score of 0-9, "mild depressive" as a score of 10-19 and "severe depressive" as a score of 20-30. Both groups were also evaluated using the Bristol Activities of Daily Living.

119 individuals were identified to participate in the study with the demographic characteristics shown in Table 1.

TABLE 1

Demographic Characteristics of AD and Normal, Healthy Controls

| | Mean Age | Gender (M/F) | MMSE | CDR | Time from Diagnosis (years) |
|---|---|---|---|---|---|
| AD (n = 100) | 70.3 (5.2) | 58/42 | 17 (9) | 2.6 (1.1) | 2.1 (1.2) |
| Controls (n = 19) | 70.6 (4.7) | 10/9 | 28 (1) | 000 | — |

Care was taken to ensure that all samples were taken within the same time of day window and in the same manner. Saliva samples were taken from the study participants by an oral physician on the day of testing from 9:00-10:00 am. Individuals were asked to abstain for eating for at least two hours prior to sample collection. Both stimulated and unstimulated samples were collected.

10 minutes prior to collection of unstimulated saliva samples, individuals were asked to rinse orally with water. At the time of sample collection, study members were asked to relax for 5-15 minutes. They were then seated in a bent forward position in an ordinary chair and asked to put their tongues on the lingual surfaces of the upper incisors and allow the saliva to drip into sterile plastic (glass) tubes treated with 50 g of 2% sodium azide solution to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minnesota) at 1800 rpm for 5 minutes to remove debris and were immediately frozen at −80° C. until further analysis.

Stimulated saliva samples were collected using the Salivette® polyester roll device (Sarstedt, Germany). The swab was placed inside the participants' mouth and they were asked to chew onto these pads for 45 s to stimulate saliva. The stimulated saliva was collected from the swab by centrifugation at 233 rcf for 2 min at 22° C. according to manufacturer's protocol. These samples were also immediately frozen at −80° C. until further analysis.

The salivary samples were evaluated for protein, flow rate and pH. Protein was analyzed using the Biuret method. Undiluted saliva was mixed with 50 g of the reagent (45 g of Rochelle salt in 400 mL of was combined with 15 g of copper sulfate while stirring. 5 g of potassium iodide was then added to the Rochelle salt/copper sulfate mixture and 0.2 N sodium hydroxide was added to make up the volume of 1 L). The absorbance of the colored product was then measured using a photoelectric colorimeter at a wavelength of 546 nm. pH was performed electrometerically using a pH meter (Hana instruments, Italy). Flow rate was calculated as the volume of saliva collected divided by the time required for collection of unstimulated saliva. Stimulated saliva was measured after a centrifuge step. Plastic cylinders containing saliva were weighed and the flow rate was calculated in g/ml (approximation of ml/min for stimulated saliva). All tests were run in duplicate.

TABLE 2

Salivary protein, flow rate and pH in AD and control subjects.

| | Controls | AD Patients Unstimulated Saliva Collection (n = 100) | AD Patients Stimulated Saliva Collection (n = 100) |
|---|---|---|---|
| Total salivary protein | 0.838 (0.245) | 0.841 (0.252) | 0.434 (0.201) |
| Flow rate | 0.398 (0.116) | 0.394 (0.114) | 0.396 (0.102) |
| pH | 6.67 (0.421) | 6.65 (0.425) | 6.86 (0.312) |

As shown in Table 2, salivary total protein, flow rate and pH levels were not significantly different between controls and AD patients.

Example II

Determination of the Optimum Set of Salivary Biomarkers for Alzheimer's Disease

Levels of Aβ-40, TNF-α, IL-1-β, Aβ-42, IGF-I, IGF-II, Alpha-amylase, cTnI, Myoglobin, MMP-9, MMP-8, MMP-2, sICAM-1, Myeloperoxidase [MPO], IL-4, IL-5, B-type natiuretic peptide [BNP], IL-1α, IL-11, IL-10, IFN-γ, VEGF, Insulin, GLP-1 (active), GLP-1 (total), TREM1, Leukotriene E4, Akt1, Fas ligand, PSA, G-CSF, MIP-1α, IL-22, IL-8, IL-21, IL-15, IL-6, IL-7, GM-CSF, IL-2, IL-17α, MCP, IL-32, RANTES, Apolipoprotein A1, Apolipoprotein D, Apolipoprotein E, Ischemia-modified albumin (IMA), Fibronectin, Aspartate aminotransferase, Lactate dehydrogenase, Tissue factor activity, MCP-1, sVCAM-1, sCD-40 were measured in the saliva of the AD individuals and control patients of Example I.

5 μl aliquots of each saliva sample were analyzed in duplicate for biomarker levels using ELISA kits according to the manufacturer's protocols. The results in Table 3 were determined by measuring the optical density of the tested samples using a spectrophotometer (Perkin-Elmer, Connecticut). MMP-2 and MMP-9 levels were quantified using kits from R&D Systems, (Minneapolis, Minn.), IL-18 using a kit from Medical & Biological Laboratories Co (Naka-ku, Nagoya, Japan), cTnI, and CD31/PCAM-1, sICAM-2, sICAM-3 (Life Diagnostic, West Chester, Pa.), sVCAM-1, BNP, RANTES (Diaclone, Besancon, Cedex, France); GM-CSF, IL-2, IL-4, IL-1α, IL-12, IL-17α, IL-1β, MCP, IL-32, IFN-γ and TNF-α (Luminex, USA); alpha amylase, aspartate aminotransferase, lactate dehygrogenase (Salimetrics, USA); MYO and MPO (Biodesign International, Saco, Me.), MCP-1 (AbD Serotec, Oxford, UK); sCD40 (HyTest Ltd, Turku, Finland); Tissue Factor Activity (St. Charles, Mo. USA) and MMP-8 (Human Quantikine, USA); Aβ-40, Aβ-42 (Biosource International, Invitrogen), IGF-I and IGF-II RIA (Van Wyk and Underwood antibody). The methods for preforming these tests as determined by the manufacturers are hereby incorporated by reference in their entirety.

TABLE 3

Comparison of Salivary Biomarker Levels in AD and Normal Healthy Individuals
Mean Value (Standard Deviation)

| Salivary Biomarker Measured | Control Samples (Normal Healthy Individuals) | Alzheimer's Disease Patients | P Value (Control and Alzheimer's Disease) |
|---|---|---|---|
| Aβ-40 (pg/ml) | 34.4 (4.56) | 12.12 (1.34) | <0.0001 |
| TNF-α (pg/ml) | 68.89 (23.78) | 267.76 (33.45) | <0.0001 |
| IL-1-β (pg/ml) | 48.56 (34.75) | 189.76 (33.89) | <0.0001 |
| Aβ-42 (pg/ml) | 4.08 (2.45) | 10.34 (1.45) | <0.0001 |
| IGF-I (ng/ml) | 2.33 (1.23) | 1.45 (0.57) | <0.0001 |
| IGF-II (ng/dL) | 3.45 (2.78) | 1.04 (0.68) | <0.0001 |
| Alpha-amylase (U/ml) | 20.2 (10.3) | 69.13 (14.51) | <0.005 |
| cTnI(ng/ml) | 1.34 (0.98) | 1.76 (1.33) | 0.578 |
| Myoglobin (ng/ml) | 0.97 (1.34) | 0.94 (0.85) | 0.893 |
| MMP-9 (ng/ml) | 73.3 (67.8) | 72.3 (67.9) | 0.582 |
| MMP-8(ng/ml) | 156.7 (145.7) | 151 (168) | 0.643 |
| MMP-2(ng/ml) | 78.4 (156.6) | 89.4 (89.4) | 0.678 |
| sICAM-1(ng/ml) | 0.78 (0.67) | 0.77 (0.72) | 0.863 |
| Myeloperoxidase [MPO] (ng/ml) | 12.45 (13.56) | 15.89 (14.67) | 0.789 |
| IL-4 (ng/ml) | 14.67 (34.56) | 14.99 (36.89) | 0.983 |
| IL-5 (ng/ml) | 23.09 (13.67) | 24.24 (24.89) | 0.544 |
| B-type natiuretic peptide [BNP] (ng/ml) | 34.78 (12.67) | 32.88 (19.56) | 0.643 |
| IL-1α (ng/ml) | 45.78 (45.78) | 44.82 (45.09) | 0.786 |
| IL-11 (ng/ml) | 78.09 (78.02) | 78.13 (73.65) | 0.632 |
| IL-10 (ng/ml) | 123.5 (67.03) | 128.4 (68.24) | 0.653 |
| IFN-γ (ng/ml) | 67.89 (34.78) | 68.34 (34.78) | 0.603 |
| VEGF (ng/ml) | 0.89 (1.23) | 0.88 (0.86) | 0.813 |
| Insulin (ng/ml) | 0.08 (0.02) | 0.05 (0.02) | 0.943 |
| GLP-1 (active) (ng/ml) | 1.34 (0.89) | 1.26 (1.34) | 0.309 |
| GLP-1 (total) (ng/ml) | 19.23 (12.03) | 19.24 (13.67) | 0.134 |
| TREM1 (ng/ml) | 13.67 (12.56) | 13.87 (14.78) | 0.894 |
| Leukotriene E4 (ng/ml) | 13.98 (13.78) | 14.89 (15.09) | 0.356 |
| Akt1 (ng/ml) | 0.83 (1.33) | 0.85 (1.03) | 0.623 |
| Fas ligand (pg/ml) | 1.34 (1.45) | 1.23 (1.34) | 0.893 |
| PSA (ng/ml) | 1.34 (1.45) | 1.32 (1.24) | 0.348 |
| G-CSF (ng/ml) | 2.45 (1.67) | 2.91 (1.63) | 0.563 |
| MIP-1α (ng/ml) | 23.67 (12.56) | 24.08 (14.89) | 0.521 |
| IL-22 (ng/ml) | 34.09 (34.09) | 35.09 (34.12) | 0.532 |
| IL-8 (ng/ml) | 123.22 (34.65) | 123.64 (45.80) | 0.634 |
| IL-21 (pg/ml) | 135.78 (67.89) | 134.22 (67.78) | 0.632 |
| IL-15 (ng/ml) | 145.89 (13.67) | 146.89 (23.78) | 0.562 |
| IL-6 (pg/ml) | 0.87 (2.2) | 0.85 (0.34) | 0.632 |
| IL-7 (ng/ml) | 13.89 (14.67) | 14.02 (14.75) | 0.763 |
| GM-CSF (ng/ml) | 90.78 (56.78) | 90.45 (56.87) | 0.825 |
| IL-2 (ng/ml) | 0.98 (1.23) | 1.02 (1.13) | 0.982 |
| IL-17α (ng/ml) | 13.78 (22.78) | 12.45 (21.43) | 0.943 |
| MCP (ng/ml) | 39.05 (22.67) | 37.85 (23.67) | 0.864 |
| IL-32 (ng/ml) | 109.45 (56.78) | 106.67 (55.78) | 0.867 |
| RANTES (ng/ml) | 67.78 (34.09) | 69.89 (34.23) | 0.653 |
| Apolipoprotein A1 (ng/ml) | 0.78 (1.32) | 0.89 (0.78) | 0.534 |
| Apolipoprotein D (ng/ml) | 0.13 (0.09) | 0.13 (0.13) | 0.563 |
| Apolipoprotein E (ng/ml) | 0.08 (0.02) | 0.07 (0.04) | 0.673 |
| Ischemia-modified albumin (IMA) (ng/ml) | 0.23 (0.98) | 0.23 (0.69) | 0.987 |
| Fibronectin(ng/ml) | 1.45 (1.09) | 1.33 (1.04) | 0.763 |
| Aspartate aminotransferase (ng/ml) | 2.45 (1.02) | 2.35 (1.06) | 0.235 |
| Lactate dehydrogenase (ng/ml) | 16.78 (10.56) | 16.78 (12.89) | 0.673 |
| Tissue factor activity (ng/ml) | 13.56 (12.34) | 14.15 (14.09) | 0.983 |
| MCP-1 (ng/ml) | 0.34 (0.67) | 0.33 (0.74) | 0.893 |
| sVCAM-1 (pg/ml) | 1.56 (0.97) | 1.57 (1.12) | 0.673 |
| sCD-40 (ng/ml) | 3.67 (1.34) | 3.77 (1.34) | 0.678 |

Figure 2:
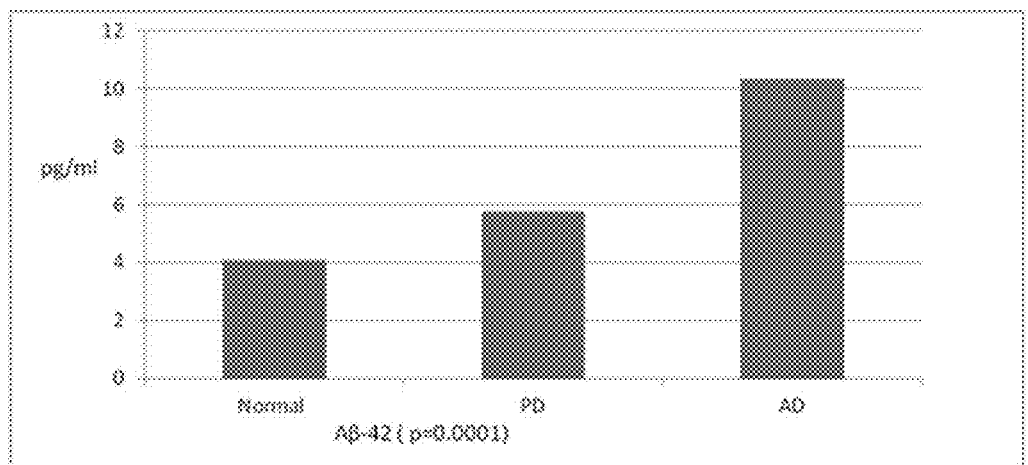
FIG. 2 is a graph comparing Aβ-42 levels in healthy individuals, individuals with AD, and individuals with PD.

As shown in Table 3 and in part in FIGS. 1 and 2, it was concluded that IGF-I, IGF-II, Aβ-40, Aβ-42, alpha amylase, IL-1β, and TNF-alpha were the best biomarkers for discriminating AD patients from controls. The results were further analyzed for discrimination between mild, moderate and severe Alzheimer's disease as shown in Table 4.

TABLE 4

Salivary Biomarker Levels in Different Types of AD and Normal Healthy Individuals
Mean Value (Standard Deviation)

| Salivary Biomarkers Measured | Control Samples (Normal Healthy Individuals) | Alzheimer's Disease Patients | | |
|---|---|---|---|---|
| | | Mild (n = 30) | Moderate (n = 35) | Severe (n = 35) |
| Aβ-40 (pg/ml) | 34.4 (4.56) | 19.17 (4.68) | 10.98 (3.56) | 5.78 (2.78) |
| TNF-α (pg/ml) | 68.89 (23.78) | 178.6 (35.23) | 231.45 (37.89) | 345.28 (67.43) |
| IL-1-β (pg/ml) | 48.56 (34.75) | 164.2 (47.89) | 196.67 (36.78) | 235.62 (56.26) |
| Aβ-42 (pg/ml) | 4.08 (2.45) | 8.21 (2.67) | 9.89 (2.13) | 15.34 (4.34) |
| IGF-I (ng/ml) | 2.33 (1.23) | 2.03 (0.89) | 1.56 (0.65) | 0.67 (0.32) |
| IGF-II (ng/dL) | 3.45 (2.78) | 1.67 (0.84) | 1.08 (0.78) | 0.56 (0.34) |
| Alpha-amylase (U/ml) | 20.2 (10.3) | 56.8 (15.6) | 68.23 (13.45) | 90.12 (34.5) |

As shown in Table 4, salivary Aβ-42, alpha amylase and IL-1 beta levels were significantly higher in AD patients than in normal patients and levels of IGF-I, IGF-II and Aβ-40 were lower in AD patients compared to control patients. Biomarker levels for Aβ-42, alpha amylase and IL-1 beta increase as the severity of the disease increases from mild to moderate to severe, but in the case of the biomarkers IGF-I, IGF-II and Aβ-40 these levels decrease as the severity of the disease increases from mild to moderate to severe (p=0.001, see Table 4) therefore quantitation of levels of salivary IGF-I, IGF-II, Aβ-40, Aβ-42, alpha amylase, IL-1 beta, and TNF-alpha biomarkers serve as useful biomarkers for differentiating the degree of AD as well as diagnosing AD.

Example III

Analysis of Diagnostic Performance of IGF-I, IGF-II, Aβ-40, Aβ-42, Alpha Amylase, IL-1β, and TNF-α

The diagnostic performance of the biomarkers to discriminate AD cases from the normal cases of Example I was evaluated using Receiver Operating Characteristic (ROC) curve analysis (Metz, 1978; Zweig & Campbell, 1993). The ROC analysis used leave-one-patient-out cross-validation (R. Kohavi, "A study of cross-validation and bootstrap for accuracy estimation and model selection," International Joint Conference on Artificial Intelligence 14, pp. 1137-1145, 1995) to assess the diagnostic performance of the classifier. Statistical comparison of populations with AD and a control population was performed using a two-tailed t-test using GraphPad Prism for Windows, v. 5.01 (GraphPad Software, San Diego, Calif.). Receiver operating characteristic curves (ROC) were generated using R(R foundation for Statistical Computing, Vienna, Austria.) As shown in Table 5, ROC analysis established the diagnostic sensitivity and specificity of the Aβ 42 biomarker at 88 and 90% respectively.

dation for Statistical Computing). Receiver operating characteristic methodology was applied to evaluate the discriminatory ability of these biomarkers between AD patients and normal controls. Thereafter, these biomarkers were subjected to decision tree analysis to find the ideal biomarker combinations and to optimize the discrimination between AD and controls using the R program.

Two different decision trees were formulated for the diagnosis of AD using AD diagnostic biomarkers. The first decision tree utilizes IGF-I, IGF-II, Aβ-40, Aβ-42, alpha amylase, IL-1 beta, and TNF-alpha levels and the second decision tree utilizes cTnI, myoglobin, MMP-9, MMP-8, MMP-2, sICAM-1 and myeloperoxidase (MPO). Specificity was calculated from the testing scores as total correctly predicted cases of AD/total number of AD cases (in this case 29/33 cases were correctly identified resulting in a calculated specificity 29/33=0.878). Specificity when applying the first decision tree was 96.2% while using the second decision tree resulted in a specificity of only 45.8%.

Example V

The Effect of Stimulated and Unstimulated Saliva on IGF-I, IGF-II, Aβ-40, Aβ-42, Alpha Amylase, IL-1 Beta, and TNF-Alpha Biomarker Levels Biomarker concentrations in saliva may be affected by the method of collection as well as the time of day of collection (Shirtcliff, 2001; Edwards 2001). Biomarker levels in stimulated and unstimulated saliva samples from the individuals selected for the study in Example I were compared to evaluate differences in collected levels. Unstimulated saliva samples were collected by a drooling technique and compared to stimulated saliva samples collected by the Salivette® polyester roll device (Sarstedt, Germany). Samples were tested by ELISA for the following biomarkers: IGF-I, IGF-II, Aβ-40, Aβ-42, alpha amylase, IL-1 beta, and TNF-alpha.

TABLE 5

ROC Analysis and Diagnostic Performance of IGF-I, IGF-II, Aβ-40, Aβ-42, Alpha Amylase, IL-1 beta, and TNF-alpha Biomarkers in Alzheimer's Disease Patients

| Parameters | Aβ-40 | Aβ-42 | IGF-I | IGF-II | Alpha Amylase | IL-1 beta | TNF-alpha |
|---|---|---|---|---|---|---|---|
| ROC AUC | 0.93 | 0.93 | 0.93 | 0.93 | 0.93 | 0.93 | 0.93 |
| Reference Value | 12 pg/ml | 5.2 pg/ml | 1.73 ng/ml | 0.62 ng/dl | 32 U/ml | 150 pg/ml | 172 pg/ml |
| Sensitivity (%) | 82 | 88 | 65 | 70 | 40 | 56 | 64 |
| Specificity (%) | 90 | 90 | 63 | 72 | 42 | 54 | 67 |
| Test Accuracy (%) | 83 | 88 | 60 | 71 | 35 | 52 | 65 |
| Positive Predictive Value (%) | 95 | 95 | 63 | 70 | 40 | 50 | 64 |
| Negative Predictive Value (%) | 64 | 75 | 62 | 70 | 42 | 53 | 67 |

Example IV

Decision Trees from AD Diagnostic Biomarker Data

The values from Example II were put into an automatic computing program and combinations of biomarkers were identified by decision tree analysis via R 2.12.1 (R Foun- 5 μl aliquots of each saliva sample were analyzed in duplicate for biomarker levels using ELISA kits according to the manufacturer's protocols. Results were determined by measuring the optical density of the tested sample using a spectrophotometer. IL-1β and TNF-α (Luminex, USA); alpha amylase, (Salimetrics, USA); Aβ-40, Aβ-42 (Biosource International, Invitrogen), IGF-I and IGF-II RIA (Van Wyk and Underwood antibody).

TABLE 6

Levels of Various Biomarkers in Unstimulated and Whole Stimulated Saliva in AD Sufferers and Normal Healthy Individuals Mean Value (Standard Deviation)

| Salivary Biomarkers Measured | Control Samples (Normal Healthy Patients) | | AD Patients | |
|---|---|---|---|---|
| | Unstimulated Whole Saliva | Stimulated Saliva | Unstimulated Whole Saliva | Stimulated Saliva |
| Aβ-40 (pg/ml) | 34.4 (4.56) | 29.74 (2.43) | 12.12 (1.34) | 8.86 (2.78) |
| TNF-α (pg/ml) | 68.89 (23.78) | 58.78 (34.56) | 267.76 (33.45) | 214.09 (45.53) |
| IL-1-β (pg/ml) | 48.56 (34.75) | 41.34 (32.67) | 189.76 (33.89) | 155.68 (43.26) |
| Aβ-42 (pg/ml) | 4.08 (2.45) | 3.78 (2.34) | 10.34 (1.45) | 8.65 (2.67) |
| IGF-I (ng/ml) | 2.33 (1.23) | 2.02 (1.12) | 1.45 (0.57) | 1.17 (0.65) |
| IGF-II (ng/dL) | 3.45 (2.78) | 3.23 (2.56) | 1.04 (0.68) | 9.3 (0.64) |
| Alpha-amylase (U/ml) | 20.2 (10.3) | 16.4 (9.7) | 69.13 (14.51) | 32.9 (12.9) |

As shown in Table 6, there were significant differences between each of the salivary biomarkers in AD patients compared to healthy controls. In certain cases the levels of the biomarkers are increased (e.g. TNF-alpha), while in other cases (e.g. IGF-I) the levels are decreased. Unstimulated whole saliva is the preferred specimen for analysis of salivary biomarkers for AD.

Example VI

Identification of Patient Population for the Determination of Parkinson's Disease Biomarkers in Saliva In order to obtain a population of Parkinson's Disease patients and a demographically matched control group, individuals from three rural clinics in Punjab, India and their family and caregivers were evaluated using the criteria of probable PD (Calne D B, Snow B J, Lee C: Criteria for diagnosing Parkinson's disease. Ann Neurol 1992, 32:125-127; Gelb D J, Oliver E, Gilman S: Diagnostic criteria for Parkinson disease. Arch Neurol 1999, 56:33-39). Subjects who Different neuropsychological batteries were used to assess cognitive functions typically affected in dementia. The core battery was taken from all subjects which has been previously described (see Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. Archives of Neurology, 49, 453-460).

In order to be included in the study, the patients had to fulfill the criteria of the United Kingdom Parkinson's Disease Society Brain Bank clinical diagnostic criteria. Individuals had to exhibit bradykinesia and at least one of: muscular rigidity, 4-6 Hz rest tremor, or postural instability not caused by primary visual, vestibular, cerebellar, or proprioceptive dysfunction. Additionally, individuals also had to have three or more of the following criteria: unilateral onset, rest tremor, progressive disorder, persistent asymmetry affecting side of onset most, excellent response (70-100%) to levodopa, severe levodopa-induced chorea, levodopa response for 5 years or more, clinical course of ten years or more. (Hughes A J, Daniel S E, Kilford L, Lees A J. Accuracy of clinical diagnosis of idiopathic Parkinson's disease. A clinico-pathological study of 100 cases. JNNP 1992; 55:181-184.)

Individuals were excluded if they met the NINCDS/ADRDA criterion for vascular dementia (McKhann G et al., Neurology 1984, 34:939-944), dementia with Lewy bodies, Non-AD dementia (i.e., frontal lobe dementia, Creutzfeldt-Jakob disease, Huntington's disease), had a history of repeated strokes with stepwise progression of Parkinsonian features, history of repeated head injury, history of definite encephalitis, oculogyric crises, neuroleptic treatment at onset of symptoms, more than one affected relative, sustained remission, strictly unilateral features after 3 years, supranuclear gaze palsy, cerebellar signs, early severe autonomic involvement, early severe dementia with disturbances of memory, language, and praxis, Babinski sign, presence of cerebral tumor or communication hydrocephalus on imaging study, negative response to large doses of levodopa in absence of malabsorption or 1-methyl-4-phenyl-1,2,3,6-tetrahydropyridine (MPTP) exposure.

Members of the control group had to match the demographics of the patients with Parkinson's disease. They additionally could not be known to suffer from dementia or other systemic diseases such as diabetes, hypertension, cardiovascular or vascular diseases. The control group was additionally evaluated using the CAMCOG and the Functional Activities Questionnaire. Both patients and members of the control group were monitored for depression using the Geriatric Depression Scale where normal was defined as a score of 0-9, "mild depressive" as a score of 10-19 and "severe depressive" as a score of 20-30. Both groups were also evaluated using the Bristol Activities of Daily Living.

51 individuals were identified to participate in the PD study with the demographic characteristics shown in Table 7. The control individuals were the same individuals identified in Example I.

TABLE 7

Demographic Characteristics of PD and Normal, Healthy Controls

| | Mean Age | Gender (M/F) | MMSE | CDR | Onset (years) |
|---|---|---|---|---|---|
| PD (n = 51) | 71.8 (4.8) | 25/26 | 18 (6) | 2.3 (1.2) | 3.4 (1.3) |
| Controls (n = 19) | 70.6 (4.7) | 10/9 | 28 (1) | 000 | — |

Saliva samples were taken from the study participants by an oral physician from 9:00-10:00 am. Individuals were asked to abstain for eating for at least two hours prior to sample collection.

10 minutes prior to collection of unstimulated saliva samples, individuals were asked to rinse orally with water. At the time of sample collection, study members were asked to relax for 5-15 minutes. They were then seated in a bent forward position in an ordinary chair and asked to put their tongues on the lingual surfaces of the upper incisors and drip into sterile plastic (glass) tubes treated with 50 g of 2% sodium azide solution to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minnesota) at 1800 rpm for 5 minutes to remove debris and were immediately frozen at −80° C. until further analysis.

Salivary samples were evaluated for protein, flow rate and pH. Protein was analyzed using the Biuret method. Undiluted saliva was mixed with the reagent (45 g of Rochelle salt in 400 mL of was combined with 15 g of copper sulfate while stirring. 5 g of potassium iodide was then added to the Rochelle salt/copper sulfate mixture and 0.2 N sodium hydroxide was added to make up the volume of 1 L). The absorbance of the colored product was then measured using a photoelectric colorimeter at a wavelength of 546 nm. pH was performed electrometerically using a pH meter. Flow rate was calculated as the volume of saliva collected divided by the time required for collection. All tests were run in duplicate.

TABLE 8

Unstimulated Salivary Protein, Flow Rate and pH in PD and Control Subjects

|  | Controls | PD Patients (n = 51) |
|---|---|---|
| Total salivary protein | 0.838 (0.245) | 0.842 (0.242) |
| Flow rate | 0.398 (0.116) | 0.399 (0.123) |
| pH | 6.67 (0.421) | 6.63 (0.433) |

As shown in Table 8, salivary total protein, flow rate and pH levels were not significantly different between controls and PD patients.

Example VII

Determination of the Optimum Set of Salivary Biomarkers for Parkinson's Disease

Salivary samples from PD individuals and control patients from Example VI were evaluated for levels of Aβ-40, TNF-α, IL-1-β, Aβ-42, IGF-I, IGF-II, Alpha-amylase, cTnI, Myoglobin, MMP-9, MMP-8, MMP-2, sICAM-1, Myeloperoxidase [MPO], IL-4, IL-5, B-type natiuretic peptide [BNP], IL-1α, IL-11, IL-10, IFN-γ, VEGF, Insulin, GLP-1 (active), GLP-1 (total), TREM1, Leukotriene E4, Akt1, Fas ligand, PSA, G-CSF, MIP-1α, IL-22, IL-8, IL-21, IL-15, IL-6, IL-7, GM-CSF, IL-2, IL-17α, MCP, IL-32, RANTES, Apolipoprotein A1, Apolipoprotein D, Apolipoprotein E, Ischemia-modified albumin (IMA), Fibronectin, Aspartate aminotransferase, Lactate dehydrogenase, Tissue factor activity, MCP-1, sVCAM-1 and sCD-40.

5 µl aliquots of each saliva sample were analyzed in duplicate for biomarker levels using ELISA kits according to the manufacturer's protocols. Results were determined by measuring the optical density of the tested sample using a spectrophotometer. MMP-2 and MMP-9 levels were quantified using kits from R&D Systems, (Minneapolis, Minn.), IL-18 using a kit from Medical & Biological Laboratories Co (Naka-ku, Nagoya, Japan), cTnI, and CD31/PCAM-1, sICAM-2, sICAM-3 (Life Diagnostic, West Chester, Pa.), sVCAM-1, BNP, RANTES (Diaclone, Besancon, Cedex, France); GM-CSF, IL-2, IL-4, IL-1α, IL-12, IL-17α, IL-1β, MCP, IL-32, IFN-γ and TNF-α (Luminex, USA); alpha amylase, aspartate aminotransferase, lactate dehygrogenase (Salimetrics, USA); MYO and MPO (Biodesign International, Saco, Me.), MCP-1 (AbD Serotec, Oxford, UK); sCD40 (HyTest Ltd, Turku, Finland); Tissue Factor Activity (St. Charles, Mo. USA) and MMP-8 (Human Quantikine, USA); Aβ-40, Aβ-42 (Biosource International, Invitrogen), IGF-I and IGF-II RIA (Van Wyk and Underwood antibody). The results of the assays are shown in Table 9 and a subset of the results are shown in FIGS. 1 and 2.

TABLE 9

Salivary Biomarkers Level in PD and Normal Healthy Individuals Mean Value (Standard Deviation)

| Salivary Biomarkers Measured | Control Samples (Normal Healthy Individuals) | Parkinson's Disease Patients | P Value (Control and Parkinson's Disease) |
|---|---|---|---|
| Aβ-40 (pg/ml) | 34.4 (4.56) | 23.6 (3.78) | <0.0001 |
| TNF-α (pg/ml) | 68.89 (23.78) | 79.89 (12.45) | <0.0001 |
| IL-1-β (pg/ml) | 48.56 (34.75) | 67.56 (24.56) | <0.0001 |
| Aβ-42 (pg/ml) | 4.08 (2.45) | 5.78 (2.34) | <0.0001 |
| IGF-I (ng/ml) | 2.33 (1.23) | 1.87 (0.97) | <0.0001 |
| IGF-II (ng/dL) | 3.45 (2.78) | 2.45 (1.78) | <0.0001 |
| Alpha-amylase (U/ml) | 20.2 (10.3) | 38.78 (10.8) | <0.005 |
| cTnI (ng/ml) | 1.34 (0.98) | 1.78 (1.32) | 0.897 |
| Myoglobin (ng/ml) | 0.97 (1.34) | 0.96 (0.89) | 0.467 |
| MMP-9 (ng/ml) | 73.3 (67.8) | 72.1 (69.2) | 0.367 |
| MMP-8 (ng/ml) | 156.7 (145.7) | 150.5 (167.8) | 0.473 |
| MMP-2 (ng/ml) | 78.4 (156.6) | 89.7 (89.3) | 0.523 |
| sICAM-1 (ng/ml) | 0.78 (0.67) | 0.78 (0.71) | 0.674 |
| Myeloperoxidase [MPO] (ng/ml) | 12.45 (13.56) | 15.67 (12.45) | 0.813 |
| IL-4 (ng/ml) | 14.67 (34.56) | 14.89 (35.78) | 0.904 |
| IL-5 (ng/ml) | 23.09 (13.67) | 22.23 (23.81) | 0.634 |
| B-type natiuretic peptide [BNP] (ng/ml) | 34.78 (12.67) | 32.89 (17.23) | 0.453 |
| IL-1α (ng/ml) | 45.78 (45.78) | 43.89 (46.89) | 0.612 |
| IL-11 (ng/ml) | 78.09 (78.02) | 77.23 (70.34) | 0.892 |
| IL-10 (ng/ml) | 123.5 (67.03) | 127.5 (69.13) | 0.922 |
| IFN-γ (ng/ml) | 67.89 (34.78) | 68.01 (35.98) | 0.632 |
| VEGF (ng/ml) | 0.89 (1.23) | 0.89 (0.87) | 0.612 |
| Insulin (ng/ml) | 0.08 (0.02) | 0.07 (0.03) | 0.678 |
| GLP-1 (active) (ng/ml) | 1.34 (0.89) | 1.24 (0.98) | 0.683 |
| GLP-1 (total) (ng/ml) | 19.23 (12.03) | 18.34 (11.22) | 0.098 |

TABLE 9-continued

Salivary Biomarkers Level in PD and Normal Healthy Individuals Mean Value (Standard Deviation)

| Salivary Biomarkers Measured | Control Samples (Normal Healthy Individuals) | Parkinson's Disease Patients | P Value (Control and Parkinson's Disease) |
|---|---|---|---|
| TREM1 (ng/ml) | 13.67 (12.56) | 13.89 (13.65) | 0.456 |
| Leukotriene E4 (ng/ml) | 13.98 (13.78) | 14.76 (14.86) | 0.782 |
| Akt1 (ng/ml) | 0.83 (1.33) | 0.84 (1.23) | 0.233 |
| Fas ligand (pg/ml) | 1.34 (1.45) | 1.33 (1.34) | 0.932 |
| PSA (ng/ml) | 1.34 (1.45) | 1.31 (1.23) | 0.785 |
| G-CSF (ng/ml) | 2.45 (1.67) | 2.89 (1.56) | 0.783 |
| MIP-1α (ng/ml) | 23.67 (12.56) | 23.98 (13.67) | 0.924 |
| IL-22 (ng/ml) | 34.09 (34.09) | 35.12 (33.12) | 0.783 |
| IL-8 (ng/ml) | 123.22 (34.65) | 122.54 (39.78) | 0.764 |
| IL-21 (pg/ml) | 135.78 (67.89) | 135.09 (64.56) | 0.664 |
| IL-15 (ng/ml) | 145.89 (13.67) | 147.99 (14.67) | 0.543 |
| IL-6 (pg/ml) | 0.87 (2.2) | 0.84 (0.97) | 0.986 |
| IL-7 (ng/ml) | 13.89 (14.67) | 13.80 (15.78) | 0.895 |
| GM-CSF (ng/ml) | 90.78 (56.78) | 90.88 (55.86) | 0.654 |
| IL-2 (ng/ml) | 0.98 (1.23) | 0.99 (1.20) | 0.548 |
| IL-17α (ng/ml) | 13.78 (22.78) | 13.89 (23.54) | 0.912 |
| MCP (ng/ml) | 39.05 (22.67) | 38.67 (22.64) | 0.904 |
| IL-32 (ng/ml) | 109.45 (56.78) | 107.34 (54.67) | 0.783 |
| RANTES (ng/ml) | 67.78 (34.09) | 69.74 (33.12) | 0.832 |
| Apolipoprotein A1 (ng/ml) | 0.78 (1.32) | 0.88 (0.78) | 0.604 |
| Apolipoprotein D (ng/ml) | 0.13 (0.09) | 0.14 (0.12) | 0.703 |
| Apolipoprotein E (ng/ml) | 0.08 (0.02) | 0.07 (0.03) | 0.956 |
| Ischemia-modified albumin (IMA) (ng/ml) | 0.23 (0.98) | 0.22 (0.67) | 0.924 |
| Fibronectin (ng/ml) | 1.45 (1.09) | 1.34 (1.03) | 0.743 |
| Aspartate aminotransferase (ng/ml) | 2.45 (1.02) | 2.34 (1.04) | 0.605 |
| Lactate dehydrogenase (ng/ml) | 16.78 (10.56) | 16.89 (12.63) | 0.894 |
| Tissue factor activity (ng/ml) | 13.56 (12.34) | 14.09 (13.56) | 0.231 |
| MCP-1 (ng/ml) | 0.34 (0.67) | 0.32 (0.75) | 0.342 |
| sVCAM-1 (pg/ml) | 1.56 (0.97) | 1.58 (1.03) | 0.453 |
| sCD-40 (ng/ml) | 3.67 (1.34) | 3.69 (1.32) | 0.367 |

Levels of IGF-I, IGF-II and Aβ-40 were lower than levels in normal healthy controls while levels of salivary Aβ-42, alpha amylase and IL-1 beta levels were higher than normal health controls. After reviewing the results shown in Table 9, it was concluded that IGF-I, IGF-II, Aβ-40, Aβ-42, alpha amylase, IL-1beta, and TNF-alpha were the best biomarkers for discriminating PD patients from the controls.

Example VIII

Analysis of Diagnostic Performance of IGF-I, IGF-II, Aβ-40, Aβ-42, Alpha Amylase, IL-1β, and TNF-α

The diagnostic performance of the biomarkers to discriminate PD cases from normal cases was evaluated using Receiver Operating Characteristic (ROC) curve analysis (Metz, 1978; Zweig & Campbell, 1993). The ROC analysis used leave-one patient-out cross validation (R. Kohavi, "A study of cross-validation and bootstrap for accuracy estimation and model selection," International Joint Conference on Artificial Intelligence 14, pp. 1137-1145, 1995) to assess the diagnostic performance of the classifier. Statistical comparison of the two populations was performed using a two-tailed t-test using GraphPad Prism for Windows, v. 5.01 (GraphPad Software, San Diego, Calif.). Receiver operating characteristic curves (ROC) were generated using R(R foundation for Statistical Computing, Vienna, Austria.)

TABLE 10

ROC Analysis and Diagnostic Performance of IGF-I, IGF-II, Aβ-40, Aβ-42, Alpha Amylase, IL-1 beta, and TNF-alpha Biomarkers in Parkinson's Disease Patients

| Parameters | Aβ-40 | Aβ-42 | IGF-I | IGF-II | Alpha Amylase | IL-1 beta | TNF-alpha |
|---|---|---|---|---|---|---|---|
| ROC AUC | 0.92 | 0.92 | 0.92 | 0.92 | 0.92 | 0.92 | 0.92 |
| Reference value | 21 pg/ml | 5.0 pg/ml | 0.90 ng/ml | 0.72 ng/dl | 27 U/ml | 62 pg/ml | 73 pg/ml |
| Sensitivity (%) | 80 | 89 | 62 | 72 | 42 | 57 | 65 |
| Specificity (%) | 95 | 95 | 62 | 73 | 40 | 55 | 67 |
| Test Accuracy (%) | 81 | 84 | 61 | 70 | 39 | 53 | 68 |
| Positive Predictive Value (%) | 95 | 95 | 65 | 71 | 38 | 52 | 66 |
| Negative Predictive Value (%) | 70 | 78 | 64 | 73 | 43 | 51 | 66 |

As shown in Table 10, ROC analysis established diagnostic sensitivity and specificity of Aβ-42 of 89% and 95%, in Parkinson's disease. The Aβ-42, Aβ-40 and IGF-II biomarkers have high diagnostic values for the diagnosis of Parkinson's disease followed by IGF-I, TNF-alpha, IL-1 beta and alpha amylase in descending order of importance.

Example IX

Analysis of the Accuracy of a Combination Biomarker Panel of Salivary IGF-I, IGF-II, Aβ-40, Aβ-42, Alpha Amylase, IL-1 Beta, and TNF-Alpha for the Diagnosis of and Discrimination Between Alzheimer's Disease and Parkinson's Disease 5 μl aliquots of saliva samples from the individuals of Example I and Example VI were analyzed using the following combinations of biomarkers: Aβ-40, Aβ-42+Aβ-40, IGF-II+Aβ-42+Aβ-40, IGF-I+IGF-II+Aβ-42+Aβ-40, TNF-alpha+IGF-I+IGF-II+Aβ-42+Aβ-40, IL-1 beta+TNF-alpha+IGF-I+IGF-II+Aβ-42+Aβ-40 amylase+IL-1 beta+TNF-alpha+IGF-I+IGF-II+Aβ-42+Aβ-40.

Statistical comparison of the two populations (AD and PD) by combination of salivary biomarkers was performed using the two-tailed t-test using GraphPad Prism for Windows, v 5.01 (GraphPad Software, San Diego, Calif.). Receiver operating characteristic curves (ROC) were generated using R(R Foundation for Statistical Computing, Vienna, Austria). Reference levels used are those described in Tables 5 and 10.

TABLE 11

ROC Analysis and Diagnostic Performance for Various Biomarker Combinations (IGF-I, IGF-II, Aβ-40, Aβ-42, Alpha Amylase, IL-1 beta, and TNF-alpha) in Alzheimer's Disease Patients

| Parameters | Aβ-40 | Aβ-42 + Aβ-40 | IGF-II + Aβ-42 + Aβ-40 | IGF-I + IGF-II + Aβ-42 + Aβ-40 | TNF-alpha + IGF-I + IGF-II + Aβ-42 + Aβ-40 | IL-1 beta + TNF-alpha + IGF-I + IGF-II + Aβ-42 + Aβ-40 | alpha amylase + IL-1 beta + TNF-alpha + IGF-I + IGF-II + Aβ-42 + Aβ-40 |
|---|---|---|---|---|---|---|---|
| ROC AUC | 0.93 | 0.93 | 0.93 | 0.93 | 0.93 | 0.93 | 0.93 |
| Sensitivity (%) | 82 | 89 | 92 | 93 | 94 | 95 | 95 |
| Specificity (%) | 90 | 92 | 94 | 95 | 96 | 96 | 96.2 |
| Test Accuracy (%) | 83 | 93 | 94 | 95 | 95 | 95.6 | 95.7 |
| Positive Predictive Value (%) | 95 | 94 | 95 | 95 | 95 | 96.2 | 96.2 |
| Negative Predictive Value (%) | 64 | 80 | 86 | 90 | 92 | 93 | 93 |

TABLE 12

ROC Analysis and Diagnostic Performance for Various Biomarker Combinations (IGF-I, IGF-II, Aβ-40, Aβ-42, Alpha Amylase, IL-1 beta, and TNF-alpha in Parkinson's disease Patients

| Parameters | Aβ-40 | Aβ-42 + Aβ-40 | IGF-II + Aβ-42 + Aβ-40 | IGF-I + IGF-II + Aβ-42 + Aβ-40 | TNF-alpha + IGF-I + IGF-II + Aβ-42 + Aβ-40 | IL-1 beta + TNF-alpha + IGF-I + IGF-II + Aβ-42 + Aβ-40 | alpha amylase + IL-1 beta + TNF-alpha + IGF-I + IGF-II + Aβ-42 + Aβ-40 |
|---|---|---|---|---|---|---|---|
| ROC AUC | 0.92 | 0.92 | 0.92 | 0.92 | 0.92 | 0.92 | 0.92 |
| Sensitivity (%) | 80 | 82 | 89 | 90 | 92 | 92 | 92 |
| Specificity (%) | 95 | 96 | 96.4 | 96.5 | 96.5 | 96.5 | 96.5 |
| Test Accuracy (%) | 81 | 86 | 87 | 89 | 90 | 90.2 | 92 |
| Positive Predictive Value (%) | 95 | 95 | 95.5 | 95.6 | 95.7 | 96 | 97 |
| Negative Predictive Value (%) | 70 | 80 | 84 | 86 | 91 | 92 | 92 |

ROC analysis established diagnostic sensitivity and specificity for Alzheimer's disease and Parkinson's disease as shown in Tables 11 and 12. The combination models of Aβ-42, Aβ-40, and IGF-II have high diagnostic values for diagnosis of Alzheimer's disease and Parkinson's disease as compared to other combination models.

Example X

Salivary Aβ-42, Aβ-40 and the Ratio of Aβ-40/Aβ-42 as Potential Biomarkers for the Diagnosis of Alzheimer's Disease and Parkinson's Disease The samples from Example I and VI were analyzed for salivary Aβ-42 and Aβ-40 using an ELISA assay (Biosource International, Invitrogen). Statistical comparison of the two diseased populations was performed using two-tailed t-test using GraphPad Prism for Windows, v 5.01 (GraphPad Software, San Diego, Calif.). Receiver operating characteristic curves (ROC) were generated using R(R Foundation for Statistical Computing, Vienna, Austria).

TABLE 13

ROC Analysis and Diagnostic Performance of Aβ-40, Aβ-42, and a Ratio of Aβ-40/Aβ-42 Biomarkers in Alzheimer's Disease

| Parameters | Aβ-40 | Aβ-42 | Aβ-40/Aβ-42 |
|---|---|---|---|
| ROC AUC | 0.93 | 0.93 | 0.98 |
| Reference Value | 21 pg/ml | 9 pg/ml | 3 |
| Sensitivity (%) | 82 | 88 | 96 |
| Specificity (%) | 90 | 90 | 90 |
| Test Accuracy (%) | 83 | 88 | 94 |
| Positive Predictive Value (%) | 95 | 95 | 96 |
| Negative Predictive Value (%) | 64 | 75 | 90 |

TABLE 14

ROC Analysis and Diagnostic Performance of Aβ-40, Aβ-42, and Ratio of Aβ-40/Aβ-42 Biomarkers in Parkinson's Disease

| Parameters | Aβ-40 | Aβ-42 | Aβ-40/Aβ-42 |
|---|---|---|---|
| ROC AUC | 0.92 | 0.92 | 0.98 |
| Reference Value | 25 pg/ml | 50 pg/ml | 0.5 |
| Sensitivity (%) | 80 | 89 | 95 |
| Specificity (%) | 95 | 95 | 95 |
| Test Accuracy (%) | 81 | 84 | 93 |
| Positive Predictive Value (%) | 95 | 95 | 95 |
| Negative Predictive Value (%) | 70 | 78 | 90 |

ROC analysis demonstrated diagnostic sensitivity and specificity of 95% and 90%, respectively (Table 13) in the case of Alzheimer's disease. Positive and negative predictive values were estimated to be near 95% and 90%, respectively, whereas the biomarkers Aβ-40 and Aβ-42 alone had negative predictive values that were equal to or less than 75% in the case of Alzheimer's disease. ROC analysis established diagnostic sensitivity and specificity of 95% and 90%, respectively (Table 14) in the case of Parkinson's disease. Positive and negative predictive values were estimated at approximately 95% and 95%, respectively, whereas Aβ-40 and Aβ-42 biomarkers alone had negative predictive values that were equal to or less than 70% in the case of Parkinson's disease. The sensitivity of salivary biomarkers Aβ-42, Aβ-40 and the ratio of Aβ-40/Aβ-42 therefore allows for early detection of Alzheimer's disease and Parkinson's disease.

Example XI

Blinded Comparative Population Analysis of AD Diagnostic Biomarkers

In order to obtain a population of Alzheimer's Disease patients and a demographically matched control group, individuals from three rural clinics in Punjab, India complaining of loss of memory and their family and caregivers were evaluated using the criteria of the Diagnostic and Statistical Manual of Mental Disorders (DSM)-IV (American Psychiatric Association: *DSM-IV. Diagnostic and Statistical Manual of Mental Disorders*. Washington D.C.: American Psychiatric Association; 1994), the Clinical Dementia Rating Scale (CDR) (Hughes, C. P., Berg, L., Danziger, W. L., et al (1982) A new clinical scale for the staging of dementia. *British Journal of Psychiatry*, 140, 566-572.), the mini-mental state examination (MMSE) (Folstein M F, Folstein S E, McHugh P R: "Mini-mental state." A practical method for grading the cognitive state of patients for the clinician. *J Psychiatr Res* 1975, 12:189-198 Alzheimer's disease specifically was evaluated using the NINCDS-ARDA criteria ((McKhann G, Drachman D, Folstein M, Katzman R, Price D, Stadlan E M: Clinical diagnosis of Alzheimer's disease: report of the NINCDS-ADRDA Work Group under the auspices of Department of Health and Human Services Task Force on Alzheimer's Disease. *Neurology* 1984, 34:939-944), and the mini-mental state examination (MMSE) was assessed for cognitive function (Folstein M F, Folstein S E, McHugh P R: "Mini-mental state". A practical method for grading the cognitive state of patients for the clinician. *J Psychiatr Res* 1975, 12:189-198), Consensus guidelines for the clinical and pathologic diagnosis of dementia with Lewy bodies (DLB): report of the consortium on DLB international workshop (McKeith, I. G., Galasko, D., Kosaka, K., et al (1996) *Neurology*, 47, 1113-1124), the Cambridge Cognitive Examination (CAMCOG) (Roth M, Tym E, Mountjoy Cq, Huppert F A, Hendrie H, Verma S, et al. CAMDEX. A standardized instrument for the diagnosis of mental disorder in the elderly with special reference to the early detection of dementia. Br J Psychiatry 1986; 149: 698-709 and Huppert, F. A., Brayne, C., Gill, C., Paykel, E. S., & Beardsall, L. (1995). CAMCOG—a concise neuropsychological test to assist dementia diagnosis: socio-demographic determinants in an elderly population sample. Br. J. Clin. Psychol. 34 (Part 4), 529-541)); the Geriatric Depression Scale (GDS) (Yesavage J A, Brink T L, Rose T L, Lum O, Huang V, Adey M, Leirer V O. Development and validation of a geriatric depression screening scale: a preliminary report. J Psychiatr Res. 1982-1983; 17(1):37-49.)); Bristol Activities of Daily Living (Bucks R S, Ashworth D L, Wilcock G K, Siegfried K. Assessment of activities of daily living in dementia: development of the Bristol Activities of Daily Living Scale. Age Ageing. 1996 March; 25(2): 113-20.)) and the Functional Activities Questionnaire (FAQ) (Pfeffer R I, Kurosaki T T, Harrah C H Jr, Chance J M, Filos S. Measurement of functional activities in older adults in the community. J Gerontol. 1982 May; 37(3):323-9.)).

In order to be included in the study, the patients had to meet the DSM-IV criterion for Alzheimer's Disease (DSM-IV-TR™ Code Number: 294.1×, 1994), the NINCDS/ADRDA criterion for "probable" or "possible Alzheimer's disease (McKhann G et al., *Neurology* 1984, 34:939-944)

and score at least one on the Clinical Dementia Rating Scale. Individuals were further evaluated using a core battery of tests as described in Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. *Archives of Neurology*, 49, 453-460. Individuals diagnosed with Alzheimer's disease had Mini Mental State Exam (MMSE) scores ranging from 14-26. Individuals were excluded if they met the NINCDS/ADRDA criterion for vascular dementia (McKhann G et al., *Neurology* 1984, 34:939-944), dementia with Lewy bodies, Non-Ad dementia (i.e., frontal lobe dementia, Creutzfelxt-Jakob disease, Huntington's disease) and any other concomitant disease.

Members of the control group had to match the demographics of the patients with Alzheimer's disease. They additionally could not be known to suffer from dementia or other systemic diseases, score more than 24 on the MMSE, or score less than 1 on the CDR scale. The control group was additionally evaluated using the CAMCOG and the Functional Activities Questionnaire. Both patients and members of the control group were monitored for depression using the Geriatric Depression Scale where normal was defined as a score of 0-9, "mild depressive" as a score of 10-19 and "severe depressive" as a score of 20-30. Both groups were also evaluated using the Bristol Activities of Daily Living.

109 individuals were identified to participate in the study with the demographic characteristics shown in Table 15 and the severity shown in Table 16.

TABLE 15

Demographic characteristics

|  | Mean Age | Gender (M/F) | MMSE | CDR | Onset (in years) |
|---|---|---|---|---|---|
| AD (n = 50) | 74.1 (4.8) | 25/25 | 20 (6) | 2.5 (1.1) | 2.8 (0.9) |
| Controls (n = 59) | 75.1 (4.4) | 27/22 | 27.9 (1.1) | 000 | — |

Care was taken to ensure that all samples were taken within a same time of day window and in the same manner. Saliva samples were taken from the study participants by an oral physician from 9:00-10:00 am (local time). Individuals were asked to abstain for eating for at least two hours prior to sample collection. Both stimulated and unstimulated samples were collected.

10 minutes prior to collection of unstimulated saliva samples, individuals were asked to rinse orally with water. At the time of sample collection, study members were asked to relax for 5-15 minutes. They then were sat in a bent forward position in an ordinary chair and asked to put their tongues on the lingual surfaces of the upper incisors and allow saliva to drip into sterile plastic (glass) tubes treated with 50 g of 2% sodium azide solution to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minnesota) at 1800 rpm for 5 minutes to remove debris and were immediately frozen at −80° C. until further analysis.

Salivary samples from AD individuals and control patients were evaluated in a blinded study for levels of A$\beta$-40 (pg/ml), TNF-$\alpha$ (pg/ml), IL-1-$\beta$ (pg/ml), A$\beta$-42 (pg/ml), IGF-I (ng/ml), IGF-II (ng/dL), Alpha-amylase (U/ml). 50 aliquots of each saliva sample were analyzed in duplicate for biomarker levels using ELISA kits according to the manufacturer's protocols. Results were determined by measuring the optical density of the tested sample using a spectrophotometer. IL-1$\beta$, and TNF-$\alpha$ (Luminex, USA); alpha amylase, (Salimetrics, USA); A$\beta$-40, A$\beta$-42 (Biosource International, Invitrogen), IGF-I and IGF-II RIA (Van Wyk and Underwood antibody).

A comparison of the relative biomarker levels in salivary specimens was made comparing control and AD groups. The results reveal the following discriminatory biomarkers: IGF-I, IGF-II, A$\beta$-40, A$\beta$-42, alpha amylase, IL-1 beta, and TNF-alpha. An unsupervised clustering (that is, the clustering algorithm that is blind to which cases are AD and which are normal) of the 40 discriminatory markers results in the clustering of the samples into 2 groups or clusters, a cluster of control samples, and a cluster of AD samples. Sensitivity in this instance was calculated as the number of correctly classified AD samples in the AD cluster divided by the total number of AD samples, which, in this particular example, is 29/32 or 90.6%.

A comparison was made between biomarker levels in the control and AD groups, revealing eight (8) biomarkers (shown in Table 17) that are differentially regulated between the two groups. Statistical analysis was performed to find the probability that the finding of differential levels was in error (the "q" value) for any one biomarker.

TABLE 17

Fold Changes for Salivary Biomarkers in AD.

| Salivary Biomarker | Fold Change | q-Value (%) |
|---|---|---|
| A$\beta$-40 (pg/ml) | 0.786 | 1.656 |
| TNF-$\alpha$ (pg/ml) | 0.778 | 1.656 |
| IL-1-$\beta$ (pg/ml) | 0.784 | 1.656 |
| A$\beta$-42 (pg/ml) | 0.867 | 1.656 |
| IGF-I (ng/ml) | 0.786 | 1.656 |
| IGF-II (ng/dL) | 0.734 | 1.656 |
| Alpha Amylase (U/ml) | 0.678 | 1.656 |

Biomarkers with differential levels and associated q values (shown as percentage values) are shown in Table 17 (fold change indicates the fold change between levels in control vs. AD samples). Sensitivity was calculated as the number of AD samples in the AD cluster divided by the total number of AD samples, which works out to be 29/32 or 90.6%. Specificity was calculated as the total correctly predicted AD number divided by the total predicted number of AD patients, which in this case is 29/34=85%.

Example XII

Sensitivity and Specificity of Salivary Biomarkers for the Diagnosis of Alzheimer's Disease A total of 100 patients at different stages of AD were selected from an outpatient department of a chosen hospital and each was enrolled in our study following receipt of ethical permission. In order to obtain a population of Alzheimer's Disease patients and a demographically matched control group, individuals from three rural clinics in Punjab, India complaining of loss of memory and their family and caregivers were evaluated using the criteria of the Diagnostic and Statistical Manual of Mental Disorders (DSM)-IV (American Psychiatric Association: *DSM-IV. Diagnostic and Statistical Manual of Mental Disorders*. Washington D.C.: American Psychiatric Association; 1994), the Clinical Dementia Rating Scale (CDR) (Hughes, C. P., Berg, L., Danziger, W. L., et al (1982) A new clinical scale for the staging of dementia. *British Journal of Psychiatry*, 140, 566-572.), the mini-mental state examination (MMSE) (Folstein M F, Folstein S E, McHugh P R: "Mini-mental state." A practical method for grading the cognitive state of patients for the clinician. *J Psychiatr Res* 1975, 12:189-198 Alzheimer's disease specifically was evaluated using the NINCDS-ARDA criteria ((McKhann G, Drachman D, Folstein M, Katzman R, Price D, Stadlan E M: Clinical diagnosis of Alzheimer's disease: report of the NINCDS-ADRDA Work Group under the auspices of Department of Health and Human Services Task Force on Alzheimer's Disease. *Neurology* 1984, 34:939-944), and the mini-mental state examination (MMSE) was assessed for cognitive function (Folstein M F, Folstein S E, McHugh P R: "Mini-mental state". A practical method for grading the cognitive state of patients for the clinician. *J Psychiatr Res* 1975, 12:189-198), Consensus guidelines for the clinical and pathologic diagnosis of dementia with Lewy bodies (DLB): report of the consortium on DLB international workshop (McKeith, I. G., Galasko, D., Kosaka, K., et al (1996) *Neurology*, 47, 1113-1124), the Cambridge Cognitive Examination (CAMCOG) (Roth M, Tym E, Mountjoy Cq, Huppert F A, Hendrie H, Verma S, et al. CAMDEX. A standardized instrument for the diagnosis of mental disorder in the elderly with special reference to the early detection of dementia. Br J Psychiatry 1986; 149: 698-709 and Huppert, F. A., Brayne, C., Gill, C., Paykel, E. S., & Beardsall, L. (1995). CAMCOG—a concise neuropsychological test to assist dementia diagnosis: sociodemographic determinants in an elderly population sample. Br. J. Clin. Psychol. 34 (Part 4), 529-541)); the Geriatric Depression Scale (GDS) (Yesavage J A, Brink T L, Rose T L, Lum O, Huang V, Adey M, Leirer V O. Development and validation of a geriatric depression screening scale: a preliminary report. J Psychiatr Res. 1982-1983; 17(1):37-49.)); Bristol Activities of Daily Living (Bucks R S, Ashworth D L, Wilcock G K, Siegfried K. Assessment of activities of daily living in dementia: development of the Bristol Activities of Daily Living Scale. Age Ageing. 1996 March; 25(2): 113-20.)) and the Functional Activities Questionnaire (FAQ) (Pfeffer R I, Kurosaki T T, Harrah C H Jr, Chance J M, Filos S. Measurement of functional activities in older adults in the community. J Gerontol. 1982 May; 37(3):323-9.)).

In order to be included in the study, the patients had to meet the DSM-IV criterion for Alzheimer's Disease (DSM-IV-TR™ Code Number: 294.1x, 1994), the NINCDS/ADRDA criterion for "probable" or "possible Alzheimer's disease (McKhann G et al., *Neurology* 1984, 34:939-944) and score at least one on the Clinical Dementia Rating Scale. Individuals were further evaluated using a core battery of tests as described in Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. *Archives of Neurology*, 49, 453-460. Individuals diagnosed with Alzheimer's disease had Mini Mental State Exam (MMSE) scores ranging from 14-26. Individuals were excluded if they met the NINCDS/ADRDA criterion for vascular dementia (McKhann G et al., *Neurology* 1984, 34:939-944), dementia with Lewy bodies, Non-AD dementia (i.e., frontal lobe dementia, Creutzfeldt-Jakob disease, Huntington's disease) and any other concomitant disease.

Members of the control group had to match the demographics of the patients with Alzheimer's disease. They additionally could not be known to suffer from dementia or other systemic diseases, score more than 24 on the MMSE, or score less than 1 on the CDR scale. The control group was additionally evaluated using the CAMCOG and the Functional Activities Questionnaire. Both patients and members of the control group were monitored for depression using the Geriatric Depression Scale where normal was defined as a score of 0-9, "mild depressive" as a score of 10-19 and "severe depressive" as a score of 20-30. Both groups were also evaluated using the Bristol Activities of Daily Living.

Salivary samples were taken and sent for analysis without knowledge of the diagnosis of patients performed by alternate methods. The following salivary biomarkers: IGF-I, IGF-II, Aβ-40, Aβ-42, alpha amylase, IL-1beta, and TNF-alpha levels were analyzed and subsequently patients were categorized according to the criteria described in Example VI in order to calculate the sensitivities and specificities for each of these specific biomarkers relevant to the diagnosis of AD.

TABLE 16

Alzheimer's Disease Severity

| | Mean Age | Gender (M/F) | MMSE | Onset (in years) |
|---|---|---|---|---|
| Mild Alzheimer's Disease (n = 36) | 70.2 (4.8) | 19/17 | 24 (2.1) | 2.1 (1.1) |
| Moderate Alzheimer's Disease (n = 34) | 70.3 (4.7) | 17/17 | 14.2 (4.4) | 2.4 (1.2) |
| Severe Alzheimer's Disease (n = 30) | 71.7 (4.5) | 15/15 | 5.3 (2.1) | 2.8 (1.2) |

Sensitivity was calculated as the number of AD samples in the AD cluster divided by the total number of AD samples, which works out to be 29/32 or 90.6%. Specificity was calculated as the total correctly predicted AD number divided by the total predicted number of AD patients, which in this case is 29/34=85%.

The sensitivities calculated for the various biomarkers (using a combination of between two and eight biomarkers) were high, ranging from 87% to 98.9%. The range of specificities was also high (from 87.5%-96.5%), therefore these biomarkers are highly applicable to the diagnosis of the different stages of AD.

Example XIII

Ratios of Aβ-42/Aβ-40 with Increased Imminent Risk for Mild Cognitive Impairment and Alzheimer's Disease Subjects in this study were 100 cognitively normal older adults forming a complete subset of those entering three clinics in Punjab, India. These individuals were registered at the three clinics as cognitively normal controls between 2006 and 2011. Cognitively normal adults were defined as community-dwelling, independently functioning individuals who were examined by a medical physician from one of the three clinics and met the following selection criteria: (1) No complaints of memory difficulties during the history taking and medical examination; (2) No active neurologic or psychiatric conditions; (3) No use of psychoactive or psychiatric medications in sufficient quantities to affect cognition; (4) Documented notation confirming that the person's memory was normal.

Individuals with a history of medical conditions or disorders that could affect cognition (e.g. head injuries) were included only if the condition was no longer active and there was no evidence of persistent or residual cognitive impairment. Individuals with current, chronic medical conditions were only included if their medical doctor judged the existing condition to be under control and not affecting cognition.

All subjects underwent baseline neurologic and neuropsychological evaluations such as the Clinical Dementia Rating (Morris J C, "The Clinical Dementia Rating (CDR): Current Version and Scoring Rules," Neurology (1993) 43: 2412-2414); Cummings J L, Mega M, Gray K, Rosenberg-Thompson S, Carusi D, Gornbein J. "The Neuropsychiatric Inventory: Comprehensive Assessment of Psychopathology in Dementia," Neurology (1994) 44: 2308-2314; Kokmen E, Smith G, Petersen R, Tangalos E, Ivnik R, "The Short Test of Mental Status: Correlations with Standardized Psychometric Testing," Arch Neurol. (1991); 48: 725-728); Hachinski V C, Lassen N A, Marshall J. "Hachinski Ischemic Index-Multi-Infarct Dementia: a Cause of Mental Deterioration in the Elderly," Lancet (1974); 2 (7874): 207-210 and "Unified Parkinson's Disease Rating Scale," In: Fahn S, Marsden C, Calne D, Golstein M, eds. "Recent Developments in Parkinson's Disease" New York, N.Y.: MacMillan Publishing Co Inc. (1987); Dementia Rating Scale (DRS) Mattis S. "Dementia Rating Scale: Psychological Assessment Resources," (1983): Auditory Verbal Learning Test: Rey A. "L' examen Psychologique dans les cas d'Encephalopathie Traumatique," Arch Psychol. (1941); 28: 286-340, Wechsler Memory Scale-Revised; Wechsler D. Wechsler "Memory Scale-Revised". New York, N.Y.: Psychological Corporation; (1987); and Wechsler Adult Intelligence Scale-Revised; Wechsler D. "Wechsler Adult Intelligence Scale-Revised". New York, N.Y.: Psychological Corporation; (1981). Study subjects were contacted yearly for re-examination. Medication lists and information regarding family history of dementia were updated at each follow-up visit. Also, the Clinical Dementia Rating, Record of Independent Living, Neuropsychiatric Inventory, Hachinski Ischemic Index, Unified Parkinson's Disease Rating Scale, Kokmen Short Test of Mental Status, and neuropsychological test battery were repeated. All baseline and follow-up examinations were reviewed at monthly consensus conferences. At baseline, entry criteria were reviewed and a Clinical Dementia Rating score of 0 was confirmed for all normal individuals enrolled in the three clinics.

The 100 individuals classified as cognitively normal then had at least 3 saliva specimens collected. Care was taken to ensure that all samples were taken within the same time of day window, and in the same manner. Each saliva sample was taken from the study participants by an oral physician from 9:00-10:00 am (time of day window). Individuals were asked to abstain for eating for at least two hours prior to unstimulated sample collection.

10 minutes prior to collection of unstimulated saliva samples, individuals were asked to rinse orally with water. At the time of sample collection, study members were asked to relax for 5-15 minutes. They then were sat in a bent forward position in an ordinary chair and asked to put their tongues on the lingual surfaces of the upper incisors and allow the saliva to drip into sterile plastic (glass) tubes treated with 50 g of 2% sodium azide solution to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minnesota) at 1800 rpm for 5 minutes to remove debris and were immediately frozen at −80° C. until further analysis.

The study participants returned to the clinics for follow up evaluations every month for five years. At each follow up visit, the participants were re-evaluated using the neurologic and neuropsychological evaluations described above. The resulting data was compared with the baseline studies to determine possible cognitive decline. Possible and probable AD was measured by standardized methods (McKhann G, Drachman D, Folstein M, Katzman R, Price D, Stadlan E.: "Clinical Diagnosis of Alzheimer's Disease: Report of the NINCDS-ADRDA Working Group Under the Auspices of the Department of Health and Human Services Task Force on Alzheimer's Disease," Neurology (1984) 34: 939-944). Subjects with abnormal clinical findings on follow-up but who did not meet the established criteria for mild cognitive impairment (MCI) or dementia were coded as having cognitive impairment of undetermined origin. More than 50% of amnestic (i.e. partial or total loss of memory) MCI cases convert to AD within 5 years. So, with a limited number of patients converting to AD, the end point was combined as incident cases of amnestic MCI and AD patients, which were initially identified during this particular study for the first time.

Twenty two (22) subjects were diagnosed as having MCI to AD during their follow-up. Of the 22 converters, 12 developed MCI, and 10 of these went on to develop AD (6 probable cases and 4 possible cases) as shown in Table 18.

TABLE 18

Five Year Follow up Diagnosis

| | Patients who Remained Normal, Healthy | Normal to Dementia | Normal to AD |
|---|---|---|---|
| Total number of subjects | 78 | 12 | 10 |
| Age, Baseline | 72.3 (3.1) | 76.2 (3.8) | 77.1 (2.9) |
| MMSE | 27.1 (2.9) | 22.9 (2.1) | 16.3 (3.1) |
| Myocardial Infarction | 10 | 6 | 8 |
| Diabetes Mellitus | 12 | 5 | 5 |
| Antihypertensive Treatment | 10 | 6 | 8 |
| Stroke | 5 | 2 | 1 |
| BMI | 27.9 (4.3) | 25.3 (3.4) | 24.2 (3.1) |

To evaluate the relationship of cognitive change to salivary Aβ-42 and Aβ-40 levels, a subgroup of individuals who had 2 Dementia Rating Scale [DRS] evaluations approximately 4 years apart and a saliva sample taken at the time of the first evaluation were identified. A window of 4 (±1) years was used for the time between DRS evaluations, and a window of ±7 months was used for the time between the initial visit and the date the saliva sample was obtained. Levels of salivary Aβ-42 and Aβ-40 were measured according to manufacturer protocols using a sandwich ELISA (Biosource International, Invitrogen). The Kaplan-Meier method was used to estimate the distribution of time to development of MCI to AD, with the time of the first collected saliva sample considered as the start of follow-up. (Kaplan, E. L.; Meier, P. (1958). "Nonparametric estimation from incomplete observations". *J. Amer. Statist. Assn.* 53 (282): 457-481. JSTOR 2281868)

The salivary Aβ-42/Aβ-40 ratio showed evidence of an association with the conversion to MCI/AD (Table 19). The risk of MCI/AD for patients with an Aβ-42/Aβ-40 ratio in the lowest quartile was estimated to be 3 times higher than the risk for subjects with a ratio in the highest quartile (P=0.01). Subjects whose Aβ-42/Aβ-40 ratio was in the lowest quartile (Q1, p<0.01) reached a 10% incidence after a period of 5 years, followed by those in Q2 who took approximately 7 years, and those in Q3 and Q4 who took approximately 10 years to reach 10% cumulative incidence where relative risk is defined as the ratio of the probability of an event occurring in an exposed group to the probability of the event occurring in a comparison, non-exposed group (Sistrom C L, Garvan C W. Proportions, odds, and risk. *Radiology* 230 (1): 12-9.)

TABLE 19

Time to MCI or AD and Salivary Aβ Ratio Measurement

| Variable | Single Variable model | |
|---|---|---|
| | Relative Risk (95% CI) | P value |
| Aβ-42/Aβ-40 | | |
| Less than the Median Quartiles | 1.68 (1.04-3.67) | 0.04 |
| Q1 | 3.87 (1.45-6.98) | 0.01 |
| Q2 | 2.97 (1.07-6.23) | |
| Q3 | 2.03 (0.98-5.99) | |
| Q4 | 1.00 | |
| Log Ratio | 1.56 (1.00-2.34) | 0.046 |
| Log Ratio Extremes Removed | 1.54 (0.86-2.56) | 0.10 |

The ratio of salivary levels of Aβ-42/Aβ-40 may therefore be used for risk detection and diagnosis of AD and MCI.

Example XIV

Comparison of Brain Autopsy Results and Salivary Biomarker Levels in Individuals Clinically Diagnosed with AD The brains of 12 individuals diagnosed with AD in Example I were evaluated according to CERAD guidelines (Mirra S S, Hart M N, Terry R D. Making the diagnosis of Alzheimer's disease. A primer for practicing pathologists. Arch Pathol Lab Med. 1993 February; 117 (2): 132-44.) and the clinical diagnosis of AD was compared to the post mortem results.

As described in Example I, each subject underwent a standard evaluation, including medical history, physical/neurological examination and a neuropsychological battery (Stern Y, Andrews H, Pittman J, et al.: "Diagnosis of Dementia in a Heterogeneous Population-Development of a Neuropsychological Paradigm-based Diagnosis of Dementia and Quantified Correction for the Effects of Education," Arch Neurol (1992) 49:453-60). All individuals were classified as having moderate Alzheimer's disease prior to their deaths.

TABLE 20

Demographic Data of 12 Individuals Assessed.

| | Mean Age | Gender (M/F) | MMSE | Onset (in Years) |
|---|---|---|---|---|
| Moderate Alzheimer's Disease | 74.2 (4.5) | 7/5 | 14.1 (4.2) | 2.5 (1.1) |

Unstimulated saliva samples were collected from all subjects at least 2-3 months before the death of the subjects. Care was taken to ensure that all samples were taken within a same time of day window and in the same manner. Saliva samples were taken from the study participants by an oral physician on the day of testing from 9:00-10:00 am. Individuals were asked to abstain for eating for at least two hours prior to sample collection. 10 minutes prior to collection of unstimulated saliva samples, individuals were asked to rinse orally with water. At the time of sample collection, study members were asked to relax for 5-15 minutes. They then were seated in a bent forward position in an ordinary chair and asked to put their tongues on the lingual surfaces of the upper incisors and allow the saliva to drip into a disposable cup held to the lower lip for 10 minutes resulting in a collection 1-5 ml of saliva per individual. Saliva samples were then centrifuged at 1800 rpm for 5 minutes to remove debris and were immediately frozen at −80° C. until further analysis.

Salivary biomarkers were measured using IGF-I and IGF-II RIA (Van Wyk and Underwood antibody), Aβ-40, Aβ-42, (Biosource International, Invitrogen), Alpha amylase, (Salimetrics, USA) IL-1 beta and TNF-alpha (Luminex, USA) sandwich ELISAs according to manufacturer protocols. Results were determined by measuring the optical density of the tested sample using a spectrophotometer.

For this study data from 12 subjects was used with moderate Alzheimer's disease who died during the study period, had detailed semi-quantitative data from brain autopsy and at least two complete assessments prior to death. Neuropathological evaluation was performed blinded to the clinical data. The brains were removed and weighed in an unfixed state, with postmortem delays ranging from 2 to 5 hours at −20 C. Each forebrain was isolated and sectioned in the midsagittal plane into two hemispheres. Both hemispheres were placed in 10% neutral buffered formalin for 5 to 7 days until further analysis. Tissue samples for diagnostic purposes were taken from different regions throughout the brainstem, cerebellum and cerebrum of the right hemisphere. Final diagnoses were made as per CERAD guidelines (Mirra S S, Hart M N, Terry R D. Making the diagnosis of Alzheimer's disease. A primer for practicing pathologists. Arch Pathol Lab Med. 1993 February; 117 (2): 132-44.)

One half-brain of each patient was assessed grossly while it was dissected in the fresh state to harvest blocks which were deep frozen and banked. The contralateral half of the brain was immersed in 10% buffered formalin phosphate solution for neuropathological evaluation, as described (Vonsattel J P, Aizawa H, Ge P, et al. "An Improved Approach to Prepare Human Brains for Research," J Neuropathol Exp Neurol (1995) 54: 42-56).

As shown in Table 21, salivary IGF-I, IGF-II, Aβ-40, Aβ-42, alpha amylase, IL-1 beta, and TNF-alpha biomarker levels in individuals diagnosed with AD were significantly different compared to normal controls from Example I.

TABLE 21

Salivary Biomarkers in Brain Autopsy Confirmed AD.

| Salivary Biomarkers Measured | Control Samples (Normal Healthy Individuals)* Unstimulated Whole Saliva | AD Patients Unstimulated Whole Saliva |
|---|---|---|
| Aβ-40 (pg/ml) | 34.4 (4.56) | 17.67 (11.70) |
| TNF-α (pg/ml) | 68.89 (23.78) | 345.12 (49.52) |
| IL-1-β (pg/ml) | 48.56 (34.75) | 178.64 (41.24) |
| Aβ-42 (pg/ml) | 4.08 (2.45) | 9.78 (1.78) |

TABLE 21-continued

Salivary Biomarkers in Brain Autopsy Confirmed AD.

| Salivary Biomarkers Measured | Control Samples (Normal Healthy Individuals)* Unstimulated Whole Saliva | AD Patients Unstimulated Whole Saliva |
| --- | --- | --- |
| IGF-I (ng/ml) | 2.33 (1.23) | 1.08 (0.56) |
| IGF-II (ng/dL) | 3.45 (2.78) | 1.89 (1.56) |
| Alpha Amylase (U/ml) | 20.2 (10.3) | 45.5 (12.4) |

*Same population as in Example II, Table 4

Quantitation of levels of salivary IGF-I, IGF-II, Aβ-40, Aβ-42, alpha amylase, IL-1 beta, and TNF-alpha biomarkers serve as useful biomarkers for the diagnosis of different types of AD.

Example XV

Levels of Salivary Biomarkers in Mild, Moderate and Severe AD and ROC Analysis and Diagnostic Performance of Various Biomarker Combinations (IGF-I, IGF-II, Aβ-40, Aβ-42, Alpha Amylase, IL-1 Beta, and TNF-Alpha) in Alzheimer's Disease Individuals admitted to three rural clinics in Punjab, India complaining of loss of memory were evaluated using the criteria of the Diagnostic and Statistical Manual of Mental Disorders (DSM)-IV (American Psychiatric Association: *DSM-IV. Diagnostic and Statistical Manual of Mental Disorders*. Washington D.C.: American Psychiatric Association; 1994), the Clinical Dementia Rating Scale (CDR) (Hughes, C. P., Berg, L., Danziger, W. L., et al (1982) A new clinical scale for the staging of dementia. *British Journal of Psychiatry*, 140, 566-572.), the mini-mental state examination (MMSE) (Folstein M F, Folstein S E, McHugh P R: "Mini-mental state." A practical method for grading the cognitive state of patients for the clinician. *J Psychiatr Res* 1975, 12:189-198), the NINCDS-ARDA criteria ((McKhann G, Drachman D, Folstein M, Katzman R, Price D, Stadlan E M: Clinical diagnosis of Alzheimer's disease: report of the NINCDS-ADRDA Work Group under the auspices of Department of Health and Human Services Task Force on Alzheimer's Disease. *Neurology* 1984, 34:939-944), the clinical Dementia Rating (CDR) scale (Hughes et al., 1982), consensus guidelines for the clinical and pathologic diagnosis of dementia with Lewy bodies (DLB): report of the consortium on DLB international workshop (McKeith, I. G., Galasko, D., Kosaka, K., et al (1996) *Neurology*, 47, 1113-1124), the Cambridge Cognitive Examination (CAMCOG) (Roth M, Tym E, Mountjoy Cq, Huppert F A, Hendrie H, Verma S, et al. CAMDEX. A standardized instrument for the diagnosis of mental disorder in the elderly with special reference to the early detection of dementia. Br J Psychiatry 1986; 149: 698-709 and Huppert, F. A., Brayne, C., Gill, C., Paykel, E. S., & Beardsall, L. (1995). CAMCOG—a concise neuropsychological test to assist dementia diagnosis: sociodemographic determinants in an elderly population sample. Br. J. Clin. Psychol. 34 (Part 4), 529-541)); the Geriatric Depression Scale (GDS) (Yesavage J A, Brink T L, Rose T L, Lum O, Huang V, Adey M, Leirer V O. Development and validation of a geriatric depression screening scale: a preliminary report. J Psychiatr Res. 1982-1983; 17(1):37-49.)); Bristol Activities of Daily Living (Bucks R S, Ashworth D L, Wilcock G K, Siegfried K. Assessment of activities of daily living in dementia: development of the Bristol Activities of Daily Living Scale. Age Ageing. 1996 March; 25(2): 113-20.)) and the Functional Activities Questionnaire (FAQ) (Pfeffer R I, Kurosaki T T, Harrah C H Jr, Chance J M, Filos S. Measurement of functional activities in older adults in the community. J Gerontol. 1982 May; 37(3):323-9.)).

In order to be included in the study, the patients had to meet the DSM-IV criterion for Alzheimer's Disease (DSM-IV-TR™ Code Number: 294.1x, 1994), the NINCDS/ADRDA criterion for "probable" or "possible Alzheimer's disease (McKhann G et al., *Neurology* 1984, 34:939-944) and score at least one on the Clinical Dementia Rating Scale. Individuals were further evaluated using a core battery of tests as described in Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. *Archives of Neurology*, 49, 453-460. 120 individuals were selected for inclusion in the study and were classified as having mild Alzheimer's disease (MMSE 21-26, n=45), Moderate Alzheimer's disease (MMSE 10-20, n=40), or severe Alzheimer's disease (MMSE less than 10, n=35). Demographics of the individuals participating in the study are shown in Table 22.

TABLE 22

Demographics and Classification of Individuals with AD

| | Mean Age | Gender (M/F) | MMSE | Onset (in years) |
| --- | --- | --- | --- | --- |
| Mild Alzheimer's Disease (n = 45) | 70.2 (4.8) | 19/17 | 24 (2.1) | 2.1 (1.1) |
| Moderate Alzheimer's Disease (n = 40) | 70.3 (4.7) | 17/17 | 14.2 (4.4) | 2.4 (1.2) |
| Severe Alzheimer's Disease (n = 35) | 71.7 (4.5) | 15/15 | 5.3 (2.1) | 2.8 (1.2) |

Saliva samples were taken from the study participants by an oral physician on the day of testing from 9:00-10:00 am. Individuals were asked to abstain for eating for at least two hours prior to sample collection. Both stimulated and unstimulated samples were collected.

10 minutes prior to collection of unstimulated saliva samples, individuals were asked to rinse orally with water. At the time of sample collection, study members were asked to relax for 5-15 minutes. They then were seated in a bent forward position in an ordinary chair and asked to put their tongues on the lingual surfaces of the upper incisors and allow the saliva to drip into a disposable cup held to the lower lip for 10 minutes resulting in a collection 1-5 ml of saliva per individual. Saliva samples were then centrifuged at 1800 rpm for 5 minutes to remove debris and were immediately frozen at −80° C. until further analysis.

Samples were ordered randomly and labeled such that the laboratories could not identify samples. 5 μl aliquots of each saliva sample were analyzed in duplicate for IL-1β, and TNF-α (Luminex, USA); alpha amylase, (Salimetrics, USA); Aβ-40, Aβ-42 (Biosource International, Invitrogen), IGF-I and IGF-II RIA (Van Wyk and Underwood antibody) biomarker levels using RIA and ELISA kits according to the manufacturer's protocols. Results were determined by measuring the optical density of the tested sample using a spectrophotometer.

The gene encoding the apolipoprotein E4 variant of the principal cholesterol carrier protein in the brain (the E4 allele of APOE) is a known risk factor for Alzheimer's disease though individuals with two copies of this gene variant comprise only about 2% of the population and only about 15% of the population carries a single copy of this version of the gene. (Goldman, Bruce Study shows common genetic factor for Alzheimer's disrupts brain function in healthy, older women, but not men, Inside Stanford Medicine). Individuals were therefore subjected to ApoE genotyping with FRET probes as described in Frances F, Portolés O, Sorlí J V, Guillén M, González J I, Corella D., Single tube optimisation of Apo E genotyping based on melting curve analysis. Clin. Biochem. 2008; 41 (10-11):923-6 to determine if biomarker levels were significantly different between individuals with and without Apo E ε4.

Example XVI

Evaluation of the Reproducibility and Stability of Salivary Biomarkers

Individuals admitted to three rural clinics in Punjab, India complaining of loss of memory were evaluated using the criteria of the Diagnostic and Statistical Manual of Mental Disorders (DSM)-IV (American Psychiatric Association: *DSM-IV. Diagnostic and Statistical Manual of Mental Disorders*. Washington D.C.: American Psychiatric Association; 1994), the Clinical Dementia Rating Scale (CDR) (Hughes, C. P., Berg, L., Danziger, W. L., et al (1982) A new clinical scale for the staging of dementia. *British Journal of Psychiatry*, 140, 566-572.), the mini-mental state examination (MMSE) (Folstein M F, Folstein S E, McHugh P R: "Mini-

TABLE 23

Levels of Various Salivary Biomarkers in Mild, Moderate and Severe Forms of Alzheimer's Disease in Individuals With and Without Apo E ε4

| | Mild Alzheimer's Disease | | Moderate Alzheimer's Disease | | Severe Alzheimer's Disease | |
|---|---|---|---|---|---|---|
| | With Apo E ε4 (n = 45) | Without Apo E ε4 (n = 30) | With Apo E ε4 (n = 40) | Without Apo E ε4 (n = 35) | With Apo E ε4 (n = 35) | Without Apo E ε4 (n = 35) |
| Aβ-40 (pg/ml) | 11.2 (1.3) | 19.17 (6.68) | 10.78 (2.12) | 10.98 (3.56) | 5.82 (1.45) | 5.78 (2.78) |
| TNF-alpha (pg/ml) | 172.6 (13.7) | 178.6 (35.23) | 235.35 (14.89) | 231.45 (37.89) | 365.34 (32.13) | 345.28 (67.43) |
| IL-1 beta (pg/ml) | 142.3 (9.4) | 164.2 (47.89) | 198.98 (21.78) | 196.67 (36.78) | 242.41 (24.12) | 235.62 (56.26) |
| Aβ-42 (pg/ml) | 5.02 (1.13) | 8.21 (2.67) | 9.98 (1.01) | 9.89 (2.13) | 16.31 (2.42) | 15.34 (4.34) |
| IGF-I (ng/ml) | 1.68 (3.8) | 2.03 (0.89) | 1.58 (0.34) | 1.56 (0.65) | 0.68 (0.13) | 0.67 (0.32) |
| IGF-II (ng/dl) | 0.62 (0.12) | 1.67 (0.84) | 1.09 (0.32) | 1.08 (0.78) | 0.57 (0.12) | 0.56 (0.34) |
| Alpha-amylase (U/ml) | 32.4 (5.8) | 56.8 (15.6) | 72.82 (5.87) | 68.23 (13.45) | 92.12 (9.01) | 90.12 (34.5) |

The area under the curve (0<AUC<1.0) represents the overall probability that the disease state being investigated of a randomly chosen subject is correctly identified by the test (Hanley, J. A. & McNeil, B. J. The meaning and use of the area under a receiver operating characteristic (ROC) curve. Radiology 143, 29-36 (1982).) These analyses are especially valuable for comparing the costs and benefits of single test measures with panels of tests that include more than one diagnostic measure or test. Thus, ROC curves can be used to interpret the interplay of the sensitivity and specificity of each candidate biomarker in isolation—and even more informatively—together with others. As shown in Table 24, combinations of IGF-I, IGF-II, Aβ-40, Aβ-42, Alpha Amylase, IL-1 beta, and TNF-alpha have an AUC of close to 1, indicating a high probability that Alzheimer's disease is correctly identified by the test.

mental state." A practical method for grading the cognitive state of patients for the clinician. *J Psychiatr Res* 1975, 12:189-198), the NINCDS-ARDA criteria ((McKhann G, Drachman D, Folstein M, Katzman R, Price D, Stadlan E M: Clinical diagnosis of Alzheimer's disease: report of the NINCDS-ADRDA Work Group under the auspices of Department of Health and Human Services Task Force on Alzheimer's Disease. *Neurology* 1984, 34:939-944), the clinical Dementia Rating (CDR) scale (Hughes et al., 1982), consensus guidelines for the clinical and pathologic diagnosis of dementia with Lewy bodies (DLB): report of the consortium on DLB international workshop (McKeith, I. G., Galasko, D., Kosaka, K., et al (1996) *Neurology*, 47, 1113-1124), the Cambridge Cognitive Examination (CAMCOG) (Roth M, Tym E, Mountjoy Cq, Huppert F A, Hendrie H, Verma S, et al. CAMDEX. A standardized instrument for the diagnosis of mental disorder in the elderly with special

TABLE 24

ROC Analysis and Diagnostic Performance of Various Biomarker Combinations (IGF-I, IGF-II, Aβ-40, Aβ-42, Alpha Amylase, IL-1 beta, and TNF-alpha) in Alzheimer's disease Patients with Apo E ε4

| Parameters | Aβ-42 | Aβ-42 + Aβ-40 | IGF-II + Aβ-42 + Aβ-40 | IGF-I + IGF-II + Aβ-42 + Aβ-40 | TNF-alpha + IGF-I + IGF-II + Aβ-42 + Aβ-40 | IL-1 beta + TNF-alpha + IGF-I + IGF-II + Aβ-42 + Aβ-40 | alpha amylase + IL-1 beta + TNF-alpha + IGF-I + IGF-II + Aβ-42 + Aβ-40 |
|---|---|---|---|---|---|---|---|
| ROC AUC | 0.95 | 0.95 | 0.95 | 0.95 | 0.95 | 0.95 | 0.95 |
| Sensitivity (%) | 70 | 78 | 89 | 98 | 98.3 | 98.4 | 99 |
| Specificity (%) | 75 | 78 | 89 | 95 | 96 | 96 | 98.2 | reference to the early detection of dementia. Br J Psychiatry 1986; 149: 698-709 and Huppert, F. A., Brayne, C., Gill, C., Paykel, E. S., & Beardsall, L. (1995). CAMCOG—a concise neuropsychological test to assist dementia diagnosis: sociodemographic determinants in an elderly population sample. Br. J. Clin. Psychol. 34 (Part 4), 529-541)); the Geriatric Depression Scale (GDS) (Yesavage J A, Brink T L, Rose T L, Lum O, Huang V, Adey M, Leirer V O. Development and validation of a geriatric depression screening scale: a preliminary report. J Psychiatr Res. 1982-1983; 17(1):37-49.)); Bristol Activities of Daily Living (Bucks R S, Ashworth D L, Wilcock G K, Siegfried K. Assessment of activities of daily living in dementia: development of the Bristol Activities of Daily Living Scale. Age Ageing. 1996 March; 25(2): 113-20.)) and the Functional Activities Questionnaire (FAQ) (Pfeffer R I, Kurosaki T T, Harrah C H Jr, Chance J M, Filos S. Measurement of functional activities in older adults in the community. J Gerontol. 1982 May; 37(3):323-9.)).

In order to be included in the study, the patients had to meet the DSM-IV criterion for Alzheimer's Disease (DSM-IV-TR™ Code Number: 294.1x, 1994), the NINCDS/ADRDA criterion for "probable" or "possible Alzheimer's disease (McKhann G et al., *Neurology* 1984, 34:939-944) and score at least one on the Clinical Dementia Rating Scale. Individuals were further evaluated using a core battery of tests as described in Stern, Y., Andrews, H., Pittman, J., Sano, M., Tatemichi T., Lantigua, R., & Mayeux, R. (1992). Diagnosis of dementia in a heterogeneous population. Development of a neuropsychological paradigm-based diagnosis of dementia and quantified correction or the effects of education. *Archives of Neurology,* 49, 453-460.

In order to be included in the study, the patients had to fulfill the criteria of the United Kingdom Parkinson's Disease Society Brain Bank clinical diagnostic criteria. Individuals had to exhibit bradykinesia and at least one of: muscular rigidity, 4-6 Hz rest tremor, or postural instability not caused by primary visual, vestibular, cerebellar, or proprioceptive dysfunction. Additionally, individuals also had to have three or more of the following criteria: unilateral onset, rest tremor, progressive disorder, persistent asymmetry affecting side of onset most, excellent response (70-100%) to levodopa, severe levodopa-induced chorea, levodopa response for 5 years or more, clinical course of ten years or more. (Hughes A J, Daniel S E, Kilford L, Lees A J. Accuracy of clinical diagnosis of idiopathic Parkinson's disease. A clinico-pathological study of 100 cases. JNNP 1992; 55:181-184.)

Individuals were excluded if they met the NINCDS/ADRDA criterion for vascular dementia (McKhann G et al., *Neurology* 1984, 34:939-944), dementia with Lewy bodies, Non-AD dementia (i.e., frontal lobe dementia, Creutzfeldt-Jakob disease, Huntington's disease), had a history of repeated strokes with stepwise progression of Parkinsonian features, history of repeated head injury, history of definite encephalitis, oculogyric crises, neuroleptic treatment at onset of symptoms, more than one affected relative, sustained remission, strictly unilateral features after 3 years, supranuclear gaze palsy, cerebellar signs, early severe autonomic involvement, early severe dementia with disturbances of memory, language, and praxis, Babinski sign, presence of cerebral tumor or communication hydrocephalus on imaging study, negative response to large doses of levodopa in absence of malabsorption or 1-methyl-4-phenyl-1,2,3,6-tetrahydropyridine (MPTP) exposure.

Members of the control group had to match the demographics of the patients with Parkinson's disease. They additionally could not be known to suffer from dementia or other systemic diseases such as diabetes hypertension, cardiovascular or vascular diseases. The control group was additionally evaluated using the CAMCOG and the Functional Activities Questionnaire. Both patients and members of the control group were monitored for depression using the Geriatric Depression Scale where normal was defined as a score of 0-9, "mild depressive" as a score of 10-19 and "severe depressive" as a score of 20-30. Both groups were also evaluated using the Bristol Activities of Daily Living.

Demographics of the individuals participating in the study are shown in Table 25.

TABLE 25

Demographics and classification of individuals with AD and PD

|  | Mean Age | MMSE | Onset (in Years) |
|---|---|---|---|
| PD | 71.6 (4.6) | 17 (8) | 2.2 (1.3) |
| Moderate Alzheimer's Disease | 70.3 (4.7) | 14.4 (4.2) | 2.3 (1.3) |

Samples were collected from 20 normal healthy, 50 AD and 20 PD patients (total 90 subjects). The samples were ordered randomly and labeled such that the laboratories could not identify the diagnosis of the individuals sampled.

For each analyte, the assay reproducibility of blinded quality control replicates was examined using the coefficient of variation (CV), a commonly used statistic to describe laboratory technical error, and determined the effect of delayed sample processing on analyte concentrations in frozen samples at −80 C (at 12 hours, 14 days and 30 days). The CV was determined by estimating the SD of the quality control values, divided by the mean of these values multiplied by 100. Between person and within person variances were estimated from repeated participant sample measurements using a random effects model, with participant ID as the random variable. Furthermore, reproducibility was assessed over a 10 and 15 day period for salivary Aβ-40, Aβ-42, IGF-I, IGF-II, alpha amylase, IL-1β, and TNF-alpha by taking samples at 10 days and 15 days without any treatment during the diagnostic process.

To assess reproducibility, the ICCs (Intraclass Correlation Coefficient) were calculated by dividing the between-person variance by the sum of the within- and between-person variances; 95% confidence intervals (CI) were also calculated. The between and within person CVs were determined by taking the square root of the between- and within-person variance components from the random effects mixed model on the ln [log] transformed scale, with approximate estimates derived by the eta method (Rosner B. Fundamentals of biostatistics. Belmont, Calif.: Duxbury; 2006). An ICC of <0.40 indicates poor reproducibility, 0.40 to 0.8 indicates fair to good reproducibility, and more than 0.8 indicates excellent reproducibility.

TABLE 26

ICCs Calculated for Delayed Analysis and Processing of Frozen Samples at 12 Hours, 14 Days and 30 Days for Various Salivary Biomarkers in Subjects. This is for all AD Types Mentioned in This Study.

| | No. of Participants/ Number of Time Points | With- Person CV (%) | Between Person CV (%) | ICC (95% CI)s |
|---|---|---|---|---|
| Aβ-40 (pg/ml) | 50/3 | 1.2 | 3.4 | 0.91 |
| TNF-alpha (pg/ml) | 50/3 | 1.2 | 3.6 | 0.89 |
| IL-1 beta (pg/ml) | 50/3 | 1.3 | 4.1 | 0.92 |
| Aβ-42 (pg/ml) | 50/3 | 1.0 | 3.2 | 0.94 |
| IGF-I (ng/ml) | 50/3 | 1.3 | 2.3 | 0.92 |
| IGF-II (ng/dl) | 50/3 | 1.4 | 2.6 | 0.93 |
| Alpha-amylase (U/ml) | 50/3 | 1.6 | 2.3 | 0.92 |

TABLE 27

ICCs Calculated at Various Time Points (Day 1, Day 10 and Day 15) in all Subjects

| | No. of Participants/ number of time points | With- Person CV (%) | Between Person CV (%) | ICC (95% CI)s |
|---|---|---|---|---|
| Aβ-40 (pg/ml) | 50/3 | 1.7 | 3.4 | 0.89 |
| TNF-alpha (pg/ml) | 50/3 | 1.8 | 3.6 | 0.87 |
| IL-1 beta (pg/ml) | 50/3 | 1.6 | 4.1 | 0.88 |
| Aβ-42 (pg/ml) | 50/3 | 1.5 | 3.2 | 0.89 |
| IGF-I (ng/ml) | 50/3 | 1.7 | 4.1 | 0.87 |
| IGF-II (ng/dl) | 50/3 | 1.6 | 4.4 | 0.88 |
| Alpha-amylase (U/ml) | 50/3 | 1.9 | 4.1 | 0.89 |

TABLE 28

ICCs Calculated for Delayed Analysis and Processing of Frozen Samples at 12 hours, 14 days and 30 days for Various Salivary Biomarkers in Subjects. This is for all PD types mentioned in this study.

| | No. of Participants/ Number of Time Points | With- Person CV (%) | Between Person CV (%) | ICC (95% CI)s |
|---|---|---|---|---|
| Aβ-40 (pg/ml) | 20/3 | 1.2 | 3.2 | 0.90 |
| TNF-alpha (pg/ml) | 20/3 | 1.3 | 3.4 | 0.86 |
| IL-1 beta (pg/ml) | 20/3 | 1.2 | 3.5 | 0.93 |
| Aβ-42 (pg/ml) | 20/3 | 1.1 | 3.1 | 0.93 |
| IGF-I (ng/ml) | 20/3 | 1.3 | 3.6 | 0.91 |
| IGF-II (ng/dl) | 20/3 | 1.3 | 3.9 | 0.92 |
| Alpha-amylase (U/ml) | 20/3 | 1.4 | 3.4 | 0.92 |

TABLE 29

ICCs Calculated at Various Time Points (Day 1, Day 10 and Day 15) in PD Subjects

| | No. of Participants/ number of time points | With- Person CV (%) | Between Person CV (%) | ICC (95% CI)s |
|---|---|---|---|---|
| Aβ-40 (pg/ml) | 20/3 | 1.8 | 3.2 | 0.87 |
| TNF-alpha (pg/ml) | 20/3 | 1.9 | 3.3 | 0.88 |
| IL-1 beta (pg/ml) | 20/3 | 1.9 | 3.9 | 0.89 |
| Aβ-42 (pg/ml) | 20/3 | 1.4 | 3.9 | 0.87 |
| IGF-I (ng/ml) | 20/3 | 1.8 | 3.8 | 0.88 |
| IGF-II (ng/dl) | 20/3 | 1.9 | 4.2 | 0.87 |
| Alpha-amylase (U/ml) | 20/3 | 1.8 | 4.1 | 0.88 |

The ICCs for the range of salivary biomarkers were high (ICCs; 0.87-0.94), indicating good to excellent reproducibility and stability.

Field Test Methods

Based on the studies discussed above, accurate field testing methods can be used by practitioners to diagnose AD and PD in the field. The methods all have the common steps of testing a saliva sample for levels of two or more of a group of biomarkers consisting of IGF-I, IGF-II, Aβ-40, Aβ-42, alpha amylase, IL-1 beta, and TNF-alpha, then determining the saliva sample is positive if levels of the group of biomarkers pass two or more criteria in a group of test criteria. For an AD test, the test criteria is if the tested levels of biomarkers are above or below (depending on the biomarker) biomarker reference levels. In some embodiments, the reference levels are those disclosed in Table 5. In other embodiments, the reference levels can be any value in a ±10% range around the reference levels disclosed in Table 5. For a PD test, the test criteria is if the tested levels of biomarkers are above or below (depending on the biomarker) biomarker reference levels. In some embodiments, the reference levels are those disclosed in Table 10. In other embodiments, the reference levels can be any value in a ±10% range around the reference levels disclosed in Table 10.

Field Test Kits

Field test kits that carry out the field test methods can be made in many forms. One embodiment of a field test kit has a set of test strips and a reading device. The set of test strips has a type of test strip for each biomarker in a group of biomarkers to be tested, such as the biomarkers in Table 3. Each type of test strip is configured to produce a fluorescence level proportional to a level present on the test strip of one of the group of biomarkers. The reading device is configured to read the fluorescence levels on each of the test strips and configured to indicate a positive result when the fluorescence levels from each of the test strips are fluorescence levels of test strips exposed to a saliva sample with levels of a group of biomarkers in the saliva sample passing one or more criteria in a group of test criteria. The test criteria can be the test criteria disclosed in the field test methods above.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

REFERENCES

1. Rajput A H, Rozdilsky B, Rajput A: Accuracy of clinical diagnosis in parkinsonism—a prospective study. *Can J Neurol Sci* 1991; 18:275-278.
2. Hughes A J, Daniel S E, Blankson S, Lees A J: A clinicopathologic study of 100 cases of Parkinson's disease. *Arch Neurol* 1993; 50:140-148.
3. Elizabeth A. Shirtcliff, Douglas A. Granger, Eve Schwartz, Mary J. Curran: Use of salivary biomarkers in biobehavioral research: cotton-based sample collection methods can interfere with salivary immunoassay results. Psychoneuroendocrinology 26 (2001) 165-173.
4. Lang A E, Lozano A M. Parkinson's disease. First of two parts. N Engl J Med. 1998; 339:1044-53.
5. Silvers A R, Som P M. Salivary glands. Radiol Clin North Am. 1998; 36:941-66.
6. Lansbury P T Jr. Back to the future: the 'old-fashioned' way to new medications for neurodegeneration. Nat Med. 2004 July; 10 Suppl:S51-7.
7. Mini Mental State Examination, by Marshal Folstein and Susan Folstein, Copyright 1975, 1998, 2001 by Mini Mental LLC, Inc.
8. Folstein et al., J. Psychiatric Research (1975): 12: 1289-198.
9. Goetz, Christopher G.; Fahn, Stanley, Martinez-Martin, Pablo, Poewe, Werner, Sampaio, Cristina, Stebbins, Glenn T., Stern, Matthew B., Tilley, Barbara C., Dodel, Richard, Dubois, Bruno, Holloway, Robert, Jankovic, Joseph, Kulisevsky, Jaime, Lang, Anthony E., Lees, Andrew, Leurgans, Sue, LeWitt, Peter A., Nyenhuis, David, Olanow, C. Warren, Rascol, Olivier, Schrag, Anette, Teresi, Jeanne A., Van Hilten, Jacobus J., LaPelle, Nancy (1 Jan. 2007). "Movement Disorder Society-sponsored revision of the Unified Parkinson's Disease Rating Scale (MDS-UPDRS): Process, format, and clinimetric testing plan". *Movement Disorders* 22 (1): 41-47.
10. Edwards S, Clow A, Evans P, Hucklebridge F. Exploration of the awakening cortisol response in relation to diurnal cortisol secretory activity. Life Sci. 2001 Mar. 23; 68(18):2093-103.
11. Kaplan, E. L.; Meier, P. (1958). "Nonparametric estimation from incomplete observations". J. Amer. Statist. Assn. 53 (282): 457-481. JSTOR 2281868.
12. Metz C E (1978) Basic principles of ROC analysis. Seminars in Nuclear Medicine 8:283-298.

What is claimed is:

1. A kit for determining whether a patient has Parkinson's disease comprising a solid support on which a plurality of agents have been affixed which in combination bind to IGF-I, IGF II, alpha amylase, and at least one or more additional biomarkers selected from the group of biomarkers consisting of Aβ40 and Aβ42 wherein each agent binds to a different single biomarker.

2. The kit of claim 1, further comprising:
instructions to take the saliva sample from the patient in a similar manner.

3. The kit of claim 1, further comprising:
instructions to take the saliva sample from the patient within a same time of day window.

4. The kit of claim 1, further comprising:
instructions to take the saliva sample from the patient in a similar manner and within a same time of day window.

* * * * *